(12) United States Patent
Schubert et al.

(10) Patent No.: US 7,531,569 B2
(45) Date of Patent: *May 12, 2009

(54) PROCESS FOR PREPARING (3-OXO-2,3-DIHYDRO-1H-ISOINDOL-1-YL) ACETYLGUANIDINE DERIVATIVES

(75) Inventors: Gerrit Schubert, Kelkheim (DE); Joerg Rieke-Zapp, Frankfurt (DE); Johannes Keil, Frankfurt (DE); Heinz-Werner Kleemann, Bischofsheim (DE); Reda Hanna, Allentown, PA (US); Bao-Guo Huang, Bridgewater, NJ (US); Xiao-Dong Wu, Bridgewater, NJ (US); Yves Gouraud, Montfermeil (FR)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/001,624

(22) Filed: Dec. 1, 2004

(65) Prior Publication Data
US 2005/0124681 A1 Jun. 9, 2005

Related U.S. Application Data

(60) Provisional application No. 60/561,652, filed on Apr. 13, 2004.

(30) Foreign Application Priority Data
Dec. 2, 2003 (DE) ................................ 103 56 717

(51) Int. Cl.
A61K 31/4035 (2006.01)
C07D 209/46 (2006.01)
C07C 229/38 (2006.01)

(52) U.S. Cl. .......................... 514/416; 548/472; 560/42
(58) Field of Classification Search ................. 514/416; 548/472, 469; 560/42
See application file for complete search history.

(56) References Cited

U.S. PATENT DOCUMENTS

| | | | |
|---|---|---|---|
| 5,231,223 A | 7/1993 | Bader et al. | |
| 6,348,476 B1 | 2/2002 | Lang | |
| 6,372,917 B1 | 4/2002 | Kleemann | |
| 6,716,840 B2 | 4/2004 | Chu et al. | |
| 6,960,582 B2 | 11/2005 | Boyce et al. | |
| 7,078,428 B2 | 7/2006 | Kleemann et al. | |
| 7,189,727 B2 | 3/2007 | Boyce et al. | |
| 2004/0048916 A1* | 3/2004 | Kleemann et al. | ........... 514/416 |
| 2004/0248895 A1 | 12/2004 | Chu et al. | |
| 2005/0124681 A1 | 6/2005 | Schubert | |
| 2006/0148880 A1 | 7/2006 | Kleemann et al. | |

FOREIGN PATENT DOCUMENTS

| | | |
|---|---|---|
| DE | 1793483 | 7/1971 |
| EP | 00208518 | 9/1991 |
| EP | 0708091 | 4/1996 |
| EP | 1424325 | 3/2003 |
| WO | WO9703951 A1 * | 2/1997 |
| WO | WO 01/77075 | 10/2001 |
| WO | 02/081443 | 10/2002 |
| WO | WO 02/081443 | 10/2002 |
| WO | WO 03/024400 | 3/2003 |
| WO | 03/101450 | 12/2003 |

OTHER PUBLICATIONS

U.S. Appl. No. 10/445,618, filed May 27, 2003, Kleemann.
March, J., Aliphatic Nucleophilic Substitution, Advanced Organic Chemistry; Third Edition, John Wiley & Sons; 1985; p. 350.
Deniau, et al., A New and Versatile Synthetic Route to 2-Dimethylamino-3-Alkyl and Arylmethylene-2,3-Dihydro-1H-Isoindol-1-ones, Tetrahedron Letters 43 (2002) 8055-8058.
U.S. Appl. No. 10/363,237, filed Jul. 18, 2001, Krauter et al.

* cited by examiner

*Primary Examiner*—Rebecca L Anderson
*Assistant Examiner*—Jason M. Nolan
(74) *Attorney, Agent, or Firm*—James W. Bolcsak

(57) ABSTRACT

A method and apparatus for preventing board warpage during the application and curing or drying of liquid epoxies, or the like, on printed circuit boards using a clamping fixture assembly, which includes at least one clamping fixture support and at least one clamping fixture overlay. If desired, a plurality of printed circuit boards may be processed using an appropriate clamping fixture assembly. Furthermore, the clamping fixture may be constructed so a slight bow or curvature thereof can counter either a convex or concave bow or curvature of the printed circuit board.

In the method, at least one printed circuit board is mounted to a clamping fixture support whereby a clamping fixture overlay is placed on top of the first printed circuit board.

18 Claims, No Drawings

PROCESS FOR PREPARING (3-OXO-2,3-DIHYDRO-1H-ISOINDOL-1-YL) ACETYLGUANIDINE DERIVATIVES

RELATED APPLICATIONS

This application claims the benefit of foreign priority under 35 U.S.C. §119(a) of German patent application No. 10356717.8, filed on Dec. 2, 2003, the contents of which are incorporated by reference herein. This application also claims the benefit of priority under 35 U.S.C. § 119(e) of U.S. Provisional Application No. 60/561,652, filed Apr. 13, 2004, the contents of which are incorporated by reference herein.

FIELD OF THE INVENTION

The present invention relates to processes for preparing (3-oxo-2,3-dihydro-1H-isoindol-1-yl)acetylguanidine derivatives via 3-hydroxy-2,3-dihydro-1H-isoindol-1-one derivatives or 3-(2-carbamoylphenyl)acrylic ester derivatives as intermediates, to a process for optical resolution, and also to intermediates of the process according to the invention.

BACKGROUND (3-Oxo-2,3-dihydro-1H-isoindol-1-yl)acetylguanidine derivatives of the formula I

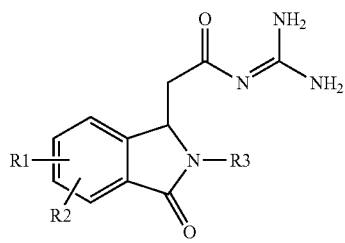

are NHE1 inhibitors and are described in PCT/EP03/05279. However, the syntheses described there lead to racemic regioisomer mixtures, which entails costly and inconvenient separation processes and reduces the yield of the desired compound. Hitherto, it has only been possible to obtain the isomers by a costly and inconvenient chromatographic separation on chiral supports. However, the substance throughput is restricted in chromatographic separations.

There is therefore a great interest in finding regioselective preparation processes for (3-oxo-2,3-dihydro-1H-isoindol-1-yl)acetylguanidine derivatives and processes for recovering the enantiomers.

DETAILED DESCRIPTION OF THE INVENTION

This need is met by the present invention. The improved, regioselective preparation of the racemic (3-oxo-2,3-dihydro-1H-isoindol-1-yl)acetylguanidine derivatives succeeds by two independent routes which are shown in scheme 1 and scheme 3. The resolution of the racemates succeeds by crystallization as the salts of 2,3-O-acylated D- or L-tartaric acids, as shown in scheme 5. Gentle base-catalyzed racemization of the in each case undesired enantiomer makes possible substantial conversion of the racemate to the desired enantiomer. The processes mentioned enable the simple preparation of enantiomerically enriched or enantiomerically pure (3-oxo-2,3-dihydro-1H-isoindol-1-yl)acetylguanidine derivatives. The novel processes now make possible the simple preparation of large amounts of substance of the compounds of the formula I on the industrial scale.

The present invention thus relates to a process for preparing compounds of the formula I

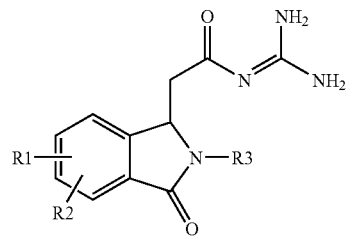

where

R1 and R2
- are each independently hydrogen, F, Cl, trifluoromethoxy, 2,2,2-trifluoroethoxy, trifluoromethyl, 2,2,2-trifluoroethyl or alkyl having 1, 2, 3 or 4 carbon atoms;

R3 is Alk-R4, trifluoromethyl;
- Alk is alkyl having 1, 2, 3 or 4 carbon atoms;
- R4 is hydrogen, trifluoromethyl or cycloalkyl having 3, 4, 5, 6 or 7 carbon atoms;

and salts thereof;

which comprises, as shown in scheme 1,

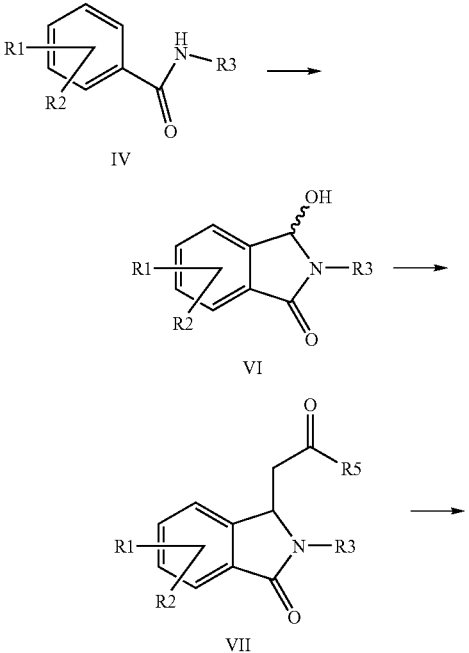

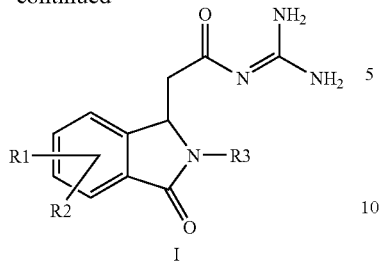

a) formylating the amide of the formula IV and then cyclizing to the compound of the formula VI,
b) reacting the compound of the formula VI with an alkoxycarbonylmethylene-triphenylphosphorane, with a 1-alkoxy-1-trimethylsiloxyethylene or with a trialkyl phosphonoacetate to give the compound of the formula VII, and
c) reacting the compound of the formula VII with guanidine to give the compound of the formula I, where, in the compounds of the formulae IV, VI and VII,
R1 to R3 are each as defined in formula I and
R5 is alkoxy having 1, 2, 3 or 4 carbon atoms;

and salts thereof.

The invention also provides a process for preparing compounds of the formula I where
R1 and R2
  are each independently hydrogen, F, Cl, trifluoromethoxy, 2,2,2-trifluoroethoxy, trifluoromethyl, 2,2,2-trifluoroethyl or alkyl having 1, 2, 3 or 4 carbon atoms;
R3 is Alk-R4, trifluoromethyl;
  Alk is alkyl having 1, 2, 3 or 4 carbon atoms;
  R4 is hydrogen, trifluoromethyl or cycloalkyl having 3, 4, 5, 6 or 7 carbon atoms;

and salts thereof;

wherein, as shown in scheme 2,

Scheme 2

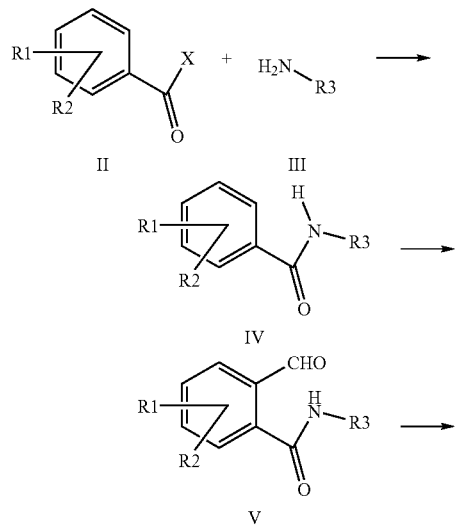

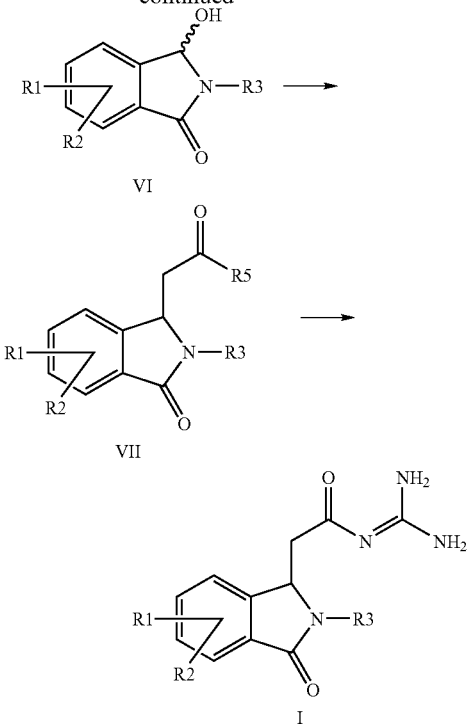

a) the compound of the formula II is reacted with the amine of the formula III to give the amide of the formula IV,
b) the amide of the formula IV is formylated at the ortho-position to the amide function to give the formyl amide of the formula V,
c) the formyl amide of the formula V is cyclized to the compound of the formula VI,
d) the compound of the formula VI is reacted with an alkoxycarbonylmethylenetriphenylphosphorane, with a 1-alkoxy-1-trimethylsiloxyethylene or with a trialkyl phosphonoacetate to give the compound of the formula VII and
e) the compound of the formula VII is reacted with guanidine to give the compound of the formula I, where, in the compounds of the formulae II, III, IV, V, VI and VII,
R1 to R3 are each as defined in formula I,
R5 is alkoxy having 1, 2, 3 or 4 carbon atoms and
X is Cl, Br, OH or alkoxy having 1, 2, 3 or 4 carbon atoms;

and salts thereof.

The compound of the formula II is typically reacted, in an inert solvent such as an ether, hydrocarbon or halogenated hydrocarbon, for example dichloromethane, at a temperature between −30° C. and the boiling point of the solvent, preferably at RT, with an amine of the formula III, if appropriate in the presence of an activating agent, to give the amide of the formula IV.

The ortho-formylation may, for example, be carried out by initially charging an alkyl-metal compound, for example an alkyllithium compound, preferably t-BuLi, with a complex ligand, preferably TMEDA, in an inert solvent such as an ether or hydrocarbon, for example THF, at a temperature between −100° C. and 0° C., preferably between −80° C. and −50° C. Then, the amide of the formula IV is added and deprotonation is effected over a period between 10 minutes and 10 hours, preferably between 10 minutes and 60 minutes, at a temperature between −100° C. and 0° C., preferably between −80° C. and −50° C. Subsequently, a formylating agent, preferably DMF, is added and reaction with the anion is effected at a temperature between −100° C. and 40° C., preferably between −80° C. and room temperature. Preference is given to leaving the solution to come to RT after addition of the DMF over a period of from 10 minutes to 3 hours, for example within 30 minutes. Amide of the formula V formed as an intermediate generally cyclizes directly to the isoindolone of the formula VI.

The isoindolone of the formula VI is reacted with a ($C_1$-$C_4$)-alkoxycarbonyl-methylenetriphenylphosphorane in an inert solvent such as an ether, hydrocarbon or halogenated hydrocarbon, for example toluene, at a temperature between 0° C. and the boiling point of the solvent, preferably between 20° C. and the boiling point of the solvent, or with a tri($C_1$-$C_4$)-alkyl phosphonoacetate in the presence of a base, for example sodium hydride, in an inert solvent such as an ether, hydrocarbon or halogenated hydrocarbon, for example 1,2-dimethoxyethane, at a temperature between 0° C. and the boiling point of the solvent, preferably between 20° C. and the boiling point of the solvent. Alternatively, the isoindolone of the formula VI is reacted with a 1-($C_1$-$C_4$)-alkyloxy-1-trimethylsiloxyethylene in the presence of a Lewis acid, for example titanium(IV) chloride or trimethylsilyl triflate, in an inert solvent such as an ether, hydrocarbon or halogenated hydrocarbon, for example dichloromethane, at a temperature between −80° C. and the boiling point of the solvent, preferably at a temperature between −80° C. and 20° C. (Synth. Commun. 1987, 17, 1).

The ester of the formula VII may be reacted by commonly known processes with guanidine to give the acylguanidine of the formula I. The reaction is preferably effected in the manner known to those skilled in the art in a protic or aprotic, polar but inert organic solvent. For example, in the reaction of the methyl ester (formula VII; R5=$OCH_3$) with guanidine, useful solvents have been found to be methanol, isopropanol or THF at temperatures of from 20° C. up to the boiling temperature of these solvents. In most reactions of compounds of the formula VII with salt-free guanidine, operation is effected, for example, in aprotic, inert solvents, for example ethers such as THF, dimethoxyethane or dioxane. However, water may also be used when use is made of a base, for example NaOH, as a solvent in the reaction of compounds of the formula VII with guanidine. In the reaction of compounds of the formula VII with salts of guanidine, for example guanidine hydrochloride, the reaction is typically effected in the presence of a base, for example potassium tert-butoxide, sodium methoxide or sodium ethoxide, in an inert solvent such as dimethylformamide, NMP, 2-propanol, at a temperature between 20° C. and the boiling point of the solvent.

In addition to the carboxylic esters of the formula VII, it is also possible to use further activated acid derivatives in the reaction with guanidine, for example carbonyl chlorides, carboxylic thioesters or carboxylic anhydrides. An activation of the carboxylic acid with, for example DCC can also be effected. The activated acid derivatives can be prepared in the manner known to those skilled in the art directly from the parent carboxylic esters of the formula VII or from the corresponding carboxylic acids which can be obtained from the esters by customary hydrolysis methods. A series of suitable methods for preparing activated carboxylic acid derivatives are specified with citation of source literature in J. March, Advanced Organic Chemistry, Third Edition (John Wiley & Sons, 1985, p. 350).

The process steps described in scheme 1 and 2 may each independently be effected continuously or batchwise. A workup of the reaction mixture may be effected at any of the process steps. The workup and, if desired, the purification of the products is effected by the customary methods such as extraction, pH separation, chromatography or crystallization and the customary dryings.

The starting compounds of the formulae II and III are commercially available or can be prepared according to or in a similar manner to the processes described in the literature and familiar to those skilled in the art.

Also claimed is a process for preparing compounds of the formula I

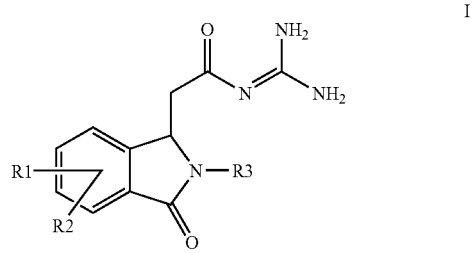

where

R1 and R2
  are each independently hydrogen, F, Cl, trifluoromethoxy, 2,2,2-trifluoroethoxy, trifluoromethyl, 2,2,2-trifluoroethyl or alkyl having 1, 2, 3 or 4 carbon atoms;

R3 is Alk-R4, trifluoromethyl;
  Alk is alkyl having 1, 2, 3 or 4 carbon atoms;
  R4 is hydrogen, trifluoromethyl or cycloalkyl having 3, 4, 5, 6 or 7 carbon atoms;

and salts thereof;

which comprises, as shown in scheme 3,

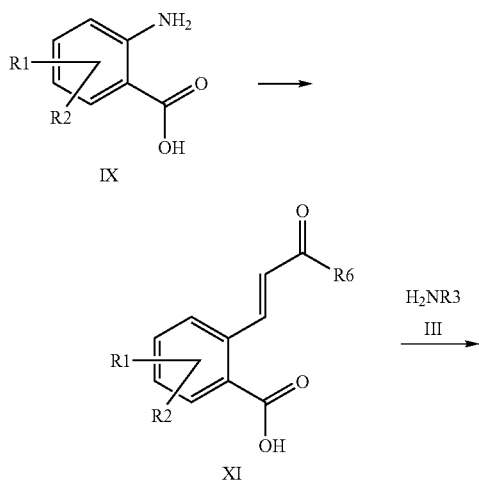

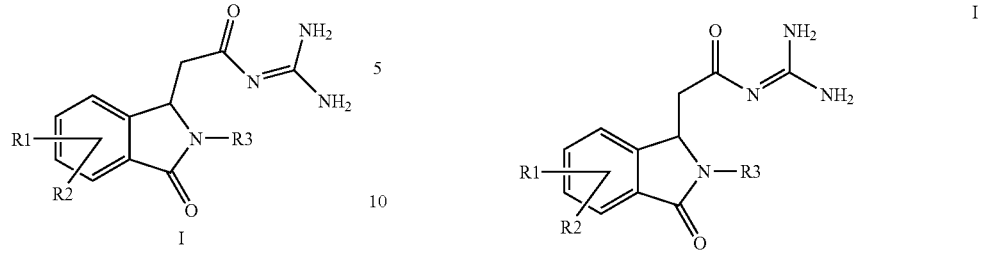

a) reacting the amine of the formula IX via a diazonium salt with an alkyl acrylate to give the cinnamic acid derivative of the formula XI,
b) reacting the compound of the formula XI with the amine of the formula III and with guanidine to give the acylguanidine of the formula I, where, in the compounds of the formulae III, IX and XI,
R1 to R3 are each as defined in formula I and
R6 is alkoxy having 1, 2, 3 or 4 carbon atoms;

and salts thereof.

The present invention also relates to a process for preparing the compounds of the formula I where
R1 and R2
    are each independently hydrogen, F, Cl, trifluoromethoxy, 2,2,2-trifluoroethoxy, trifluoromethyl, 2,2,2-trifluoroethyl or alkyl having 1, 2, 3 or 4 carbon atoms;
R3 is Alk-R4, trifluoromethyl;
    Alk is alkyl having 1, 2, 3 or 4 carbon atoms;
    R4 is hydrogen, trifluoromethyl or cycloalkyl having 3, 4, 5, 6 or 7 carbon atoms;

and salts thereof;

wherein, as shown in scheme 4,

Scheme 4

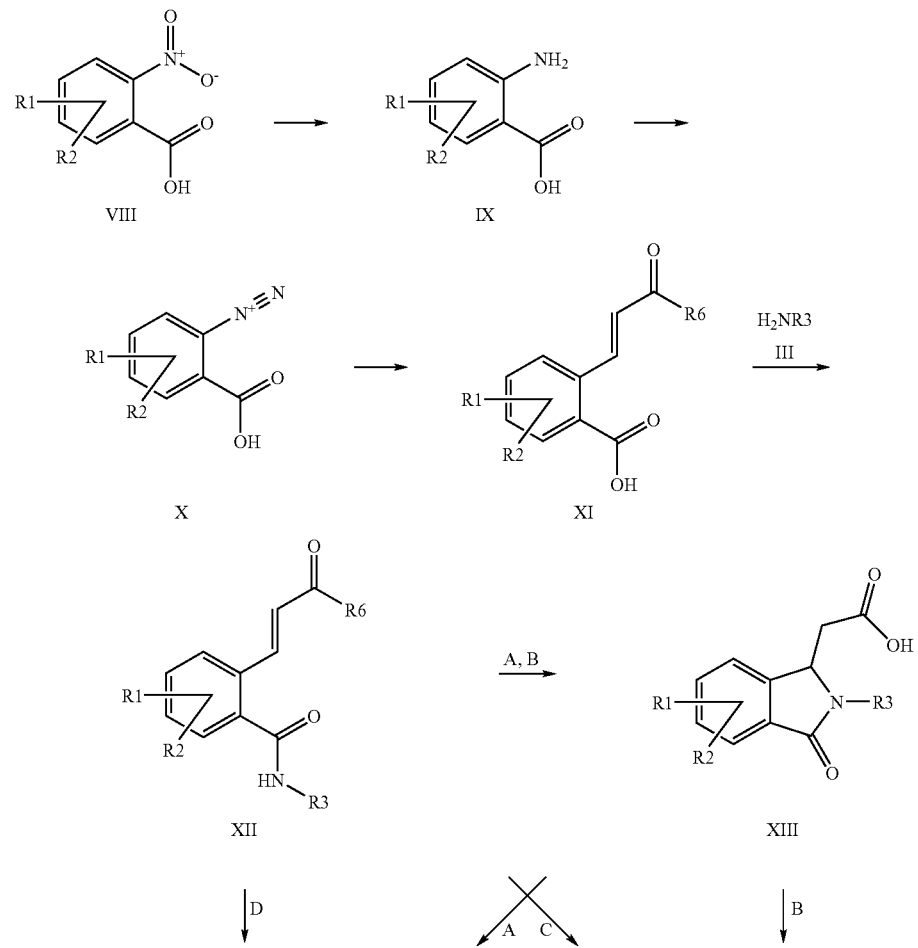

-continued

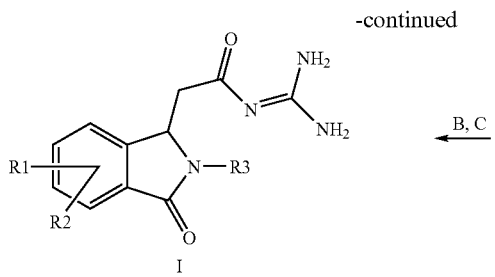

I

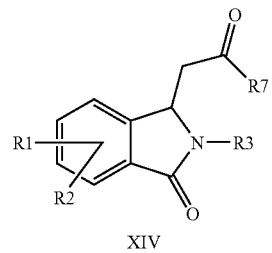

XIV a) the nitro compounds of the formula VIII is converted to the amine of the formula IX,
b) the amine of the formula IX is converted to the diazonium salt of the formula X,
c) the diazonium salt of the formula X is reacted with an alkyl acrylate to give the cinnamic acid derivative of the formula XI,
d) the compound of the formula XI is converted to the amide of the formula XII and
e) the compound of the formula XII is converted to the acylguanidine of the formula I, either by converting the compound of the formula XII in the presence of a base to the isoindolone derivative of the formula XIII and subsequently by reaction with guanidine with activation to give the acylguanidine of the formula I (alternative A), or, after formation of the isoindolone derivative of the formula XIII, in the presence of a base, from the compound of the formula XII, by converting the compound of the formula XIII to the ester of the formula XIV and subsequently by reacting with guanidine to give the acylguanidine of the formula I (alternative B), or by converting the compound of the formula XII in the presence of a strong base to the ester of the formula XIV and subsequently by reacting with guanidine to the acylguanidine of the formula I (alternative C), or by directly reacting the compound of the formula XII with guanidine in the presence of a base with simultaneously proceeding guanylation and cyclization to give the isoindolone of the formula I (alternative D), where, in the compounds of the formulae VII, IX, X, XI, XII, XIII and XIV,
R1 to R3 are each as defined in formula I and
R6 and R7 are each independently alkoxy having 1, 2, 3 or 4 carbon atoms;

and salts thereof.

The nitro compounds of the formula VIII may be reduced by known methods (for example described in "Houben-Weyl, Methoden der organischen Chemie", Volume XI/1, Nitrogen compounds II, Georg Thieme Verlag Stuttgart, 1957, p. 360ff) to the aniline of the formula IX. Preference is given to catalytic hydrogenation, for example using Pd/C, for example using 5% Pd/C or 10% Pd/C, in a solvent, for example an alcohol, preferably ethanol, under a hydrogen atmosphere of from 1 bar to 200 bar pressure, preferably from 1 bar to 10 bar of pressure.

The subsequent diazotization of the aniline of the formula IX is effected in an inert solvent, preferably ethanol, in the presence of an acid whose anion does not substitute the diazonium ion itself, for example $HBF_4$ or $HPF_6$, preferably $HBF_4$, or, for example, $H_2SO_4$ and in the presence of a nitrite, preferably $NaNO_2$, at a temperature between $-30°$ C. and the boiling point of the solvent, preferably between $0°$ C. and $30°$ C.

The diazonium salt of the formula X is preferably reacted directly with a ($C_1$-$C_4$)-alkyl acrylate, preferably ethyl acrylate, in the presence of a palladium catalyst, preferably $Pd(OAc)_2$, at a temperature between $0°$ C. and the boiling point of the solvent, preferably between $45°$ C. to $55°$ C., to give the cinnamic acid derivative of the formula XI.

The benzoic acid function of the compound of the formula XI may be converted to the amide of the formula XII by methods known to those skilled in the art, preferably via the acid chloride or with the aid of DCC. This reaction may also be conducted in such a way that the amide of the formula XII is cyclized in the reaction mixture directly to the ester of the formula XIV, i.e. the reaction of the compound of the formula XI to give the ester of the formula XIV is carried out in one step. This may be done either under the basic reaction conditions of amide formation or the cyclization may be brought about by adding a base, for example triethylamine, Hünig's base or potassium tert-butoxide. A further alternative consists in converting the compound of the formula XI directly to the compound of the formula I by successively carrying out amide formation, cyclization and guanidation in the same reaction vessel, in which case the reaction may be effected without isolating intermediates.

For the further conversion of the compound of the formula XII to the acylguanidine of the formula I there are 4 alternatives:

Alternative A: The conversion of the amide of the formula XI is preferably effected using aqueous alkali solution, preferably aqueous NaOH solution, in a solvent such as an alcohol, preferably methanol or ethanol, at a temperature between $-30°$ C. and the boiling point of the solvent, preferably at RT. Both the hydrolysis of the ester function and the cyclization to the isoindolone derivative of the formula XIII take place. The compound of the formula XIII is activated for acylation by commonly known processes (and as described for scheme 1), for example using the acid chloride or with DCC, and the acylguanidine of the formula I is obtained.

Alternative B: As in alternative A, the carboxylic acid of the formula XIII is synthesized. Subsequently, standard processes for ester preparation, preferably using $SOCl_2$ in an alcohol such as methanol or ethanol, are used to prepare, for example, the methyl or ethyl ester of the formula XIV. The ester of the formula XIV is subsequently converted to the acylguanidine of the formula I as described for scheme 1.

Alternative C: The conversion of the amide of the formula XII is effected in a solution of a strong base, preferably methoxide or t-butoxide in an alcohol such as methanol or ethanol, and the methyl or ethyl ester of the formula XIV is obtained. The conversion of the ester of the formula XIV to the acylguanidine of the formula I is effected as described for scheme 1.

Alternative D: The amide of the formula XII is converted under customary conditions for the acylation of guanidine. The solvent used is an inert solvent such as an ether, hydrocarbon or halogenated hydrocarbon, preferably DMF. Typically, a guanidinium salt is initially reacted with a strong base, preferably KOtBu, which releases the free guanidine. The mixture is added to the solution of the compound of the formula XII in a solvent such as an alcohol, ether, hydrocarbon or halogenated hydrocarbon, for example DMF, NMP or 2-propanol. In the course of the addition, the guanylation and the cyclization to the isoindolone of the formula I occurs simultaneously. In one variant, the compound of the formula M is cyclized to the compound of the formula MV and then converted in situ to the compound of the formula I successively in time using a catalytic amount of a strong base, for example potassium tert-butoxide or sodium methoxide or sodium ethoxide, in a solvent, for example DMF, NMP or 2-propanol.

Preference is given to alternative D in which the conversion of the benzoic acid derivative of the formula XI is carried out in a one-pot process to give acylguanidine of the formula I.

The process steps described in scheme 2 may be effected continuously or batchwise. A workup of the reaction mixture may be effected after any of the process steps. The workup and, if desired, the purification of the products is effected by the customary methods such as extraction, pH separation, chromatography or crystallization and the customary dryings.

The starting compounds of the formulae III and VIII are commercially available or can be prepared according to or in a similar manner to the processes described in the literature and known to those skilled in the art.

The invention also provides compounds of the formula XII

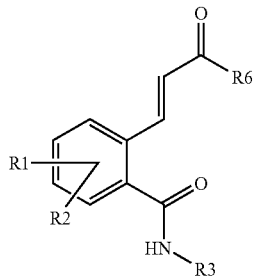

where

R1 and R2
are each independently hydrogen, F, Cl, trifluoromethoxy, 2,2,2-trifluoroethoxy, trifluoromethyl, 2,2,2-trifluoroethyl or alkyl having 1, 2, 3 or 4 carbon atoms;

R3 is Alk-R4, trifluoromethyl;

Alk is alkyl having 1, 2, 3 or 4 carbon atoms;

R4 is hydrogen, trifluoromethyl or cycloalkyl having 3, 4, 5, 6 or 7 carbon atoms;

R6 is alkoxy having 1, 2, 3 or 4 carbon atoms;

and salts thereof.

Also claimed is the use of the compounds of the formula XII as a synthetic intermediate.

Compounds of the formula I in enantiomerically enriched or in enantiomerically pure form may advantageously be prepared by a novel optical resolution process which likewise forms part of the subject matter of the present invention. To this end, the racemates of the compounds of the formula I are crystallized as salts of 2,3-O-acylated D- or L-tartaric acid, in the course of which the enantiomers are enriched in the crystal or in the mother liquor. Subsequently, the free bases are released again from the salts.

The present invention thus relates to a process for isolating compounds of the formula Ia and Ib

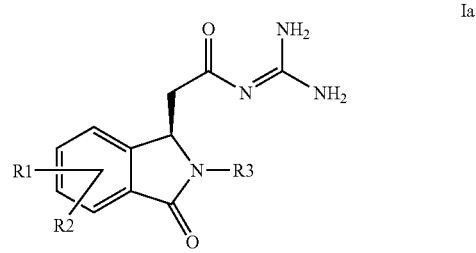

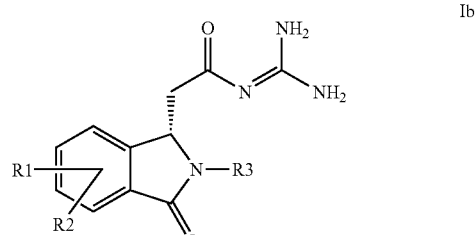

where

R1 and R2
are each independently hydrogen, F, Cl, trifluoromethoxy, 2,2,2-trifluoroethoxy, trifluoromethyl, 2,2,2-trifluoroethyl or alkyl having 1, 2, 3 or 4 carbon atoms;

R3 is Alk-R4, trifluoromethyl;

Alk is alkyl having 1, 2, 3 or 4 carbon atoms;

R4 is hydrogen, trifluoromethyl or cycloalkyl having 3, 4, 5, 6 or 7 carbon atoms;

and salts thereof;

which comprises, as shown in scheme 5,

Scheme 5

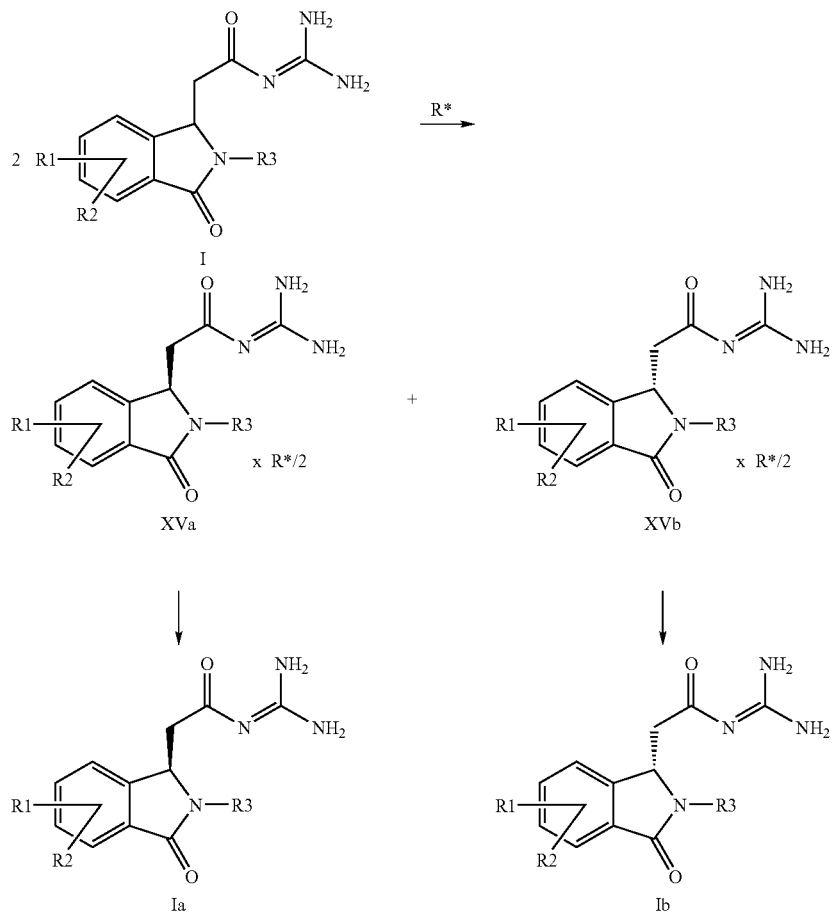

a) converting the compound of the formula I to salts of a 2,3-O-acylated D- or L-tartaric acid and obtaining the two salts of the formulae XVa and XVb separately by crystallization, and
b) releasing the free bases of the formulae Ia and Ib from the two salts of the formulae XVa and XVb respectively, where, in the compounds of the formulae I, XVa and XVb, R1 to R3 are each as defined in the formulae Ia and Ib
R* is

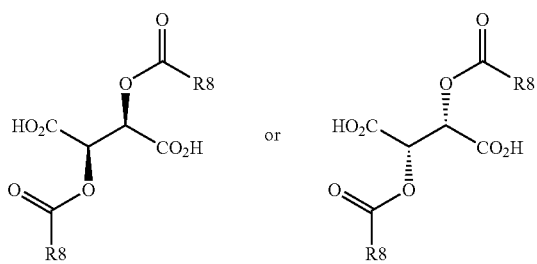

R8 is alkyl having 1, 2, 3, 4, 5 or 6 carbon atoms or phenyl which is unsubstituted or substituted by 1, 2 or 3 substituents from the group of F, Cl, Br, I, alkyl having 1, 2, 3 or 4 carbon atoms or alkoxy having 1, 2, 3 or 4 carbon atoms.

Also claimed is the above-described process in which the undesired enantiomer of the formula Ia or Ib is racemized again.

The racemate of the compound of the formula I is crystallized with a tartaric acid derivative R*, for example O,O'-dibenzoyl-D-tartaric acid, O,O'-dibenzoyl-L-tartaric acid, O,O'-di(4-methylbenzoyl)-L-tartaric acid, O,O'-di(4-methylbenzoyl)-D-tartaric acid, O,O'-di(4-methoxybenzoyl)-L-tartaric acid or O,O'-di(4-methoxybenzoyl)-D-tartaric acid, preferably with O,O'-dibenzoyl-L-tartaric acid or O,O'-dibenzoyl-D-tartaric acid, in a suitable solvent, for example in an ether, e.g. diethyl ether, diisopropyl ether, dimethoxyethane, tetrahydrofuran or dioxane, in a halogenated hydrocarbon, e.g. dichloromethane, trichloromethane, tetrachloromethane, 1,2-dichloromethane or trichloroethylene, in an alcohol, e.g. methanol, ethanol, n-propanol, 2-propanol, butanol, in an ester, e.g. ethyl acetate or butyl acetate, in water, or in mixtures of solvents, preferably in 2-propanol, dimethoxyethane or ethyl acetate, at a temperature between −10° C. and the boiling point of the solvent, preferably at from 0° C. to 40° C. In one variant of the process, mixtures of two or more 2,3-O-acylated D- or L-tartaric acids of the same configuration which bear different acyl groups are used for the separation.

The salt formation from the compound of the formula I and the tartaric acid derivative R* can be effected using equivalent amounts, i.e. 0.5 mol of the tartaric acid derivative R* which contains two carboxylic acid groups may be used per mole of the compound of the formula I. However, the compound of the formula I may also be crystallized with less than 0.5 mol equivalent of the 2,3-O-acylated D- or L-tartaric acid, for example with from 0.25 mol to 0.5 mol of tartaric acid derivative R* per mole of the compound of the formula I, in particular with from 0.25 mol to 0.3 mol of tartaric acid derivative R* per mole of the compound of the formula I. The desired enantiomer then crystallizes out in the form of the salt of the formula XVa or XVb and the undesired enantiomer is for the most part present in the mother liquor in the form of the enantiomers of the formula Ib or Ia and not in the form of the salt of the formula XVa or XVb. The enantiomeric purity of the salts of the formulae XVa and XVb may be increased by repeated crystallization or by stirring of the first crystals with fresh solvent at elevated temperature and subsequent cooling.

After separation of the two salts of the formulae XVa and XVb and separation of the salt of the formula XVa or XVb from the undesired enantiomer Ib or Ia, the enantiomerically enriched compounds of the formulae Ia and Ib are subsequently typically released from the salts by addition of an auxiliary base, for example an amine, e.g. triethylamine, an inorganic base such as $NaHCO_3$, $Na_2CO_3$ or aqueous solutions thereof. It is customary to work in a suitable solvent, for example in an ether, e.g. diethyl ether, diisopropyl ether, dimethoxyethane, tetrahydrofuran or dioxane, in a halogenated hydrocarbon, e.g. dichloromethane, trichloromethane, tetrachloromethane, 1,2-dichloroethane or trichloroethylene, in an alcohol, e.g. methanol, ethanol, n-propanol, 2-propanol or butanol, in an ester, e.g. ethyl acetate or butyl acetate, or in water or in solvent mixtures, preferably in ethyl acetate, 2-propanol, dichloromethane or water or mixtures thereof, in which case the reaction mixture may have one or more phases, at a temperature between −10° C. and the boiling point of the solvent, preferably at from 10° C. to 40° C. This may be done, for example, in such a way that the salt is dissolved in aqueous $NaHCO_3$ solution and the enantiomer of the formula Ia or Ib is then extracted using an organic solvent, for example ethyl acetate.

The enantiomer Ia or Ib which is undesired in each case may be converted back to the racemate of the formula I by a racemization process and is thus available for another optical resolution step. In this case, the undesired enantiomer is preferably treated in a solvent such as an alcohol, e.g. 2-propanol, at a temperature between −10° C. and the boiling point of the solvent, preferably at from 0° C. to 40° C., with small amounts of a base, for example KOH, the reaction mixture is neutralized and the racemate is isolated after aqueous-extractive workup. This process may be carried out by suitable selection of the amount of base and reaction temperature in such a way that virtually exclusively racemization and no chemical change in the substance occurs.

The present invention also provides compounds of the formulae XVa and XVb

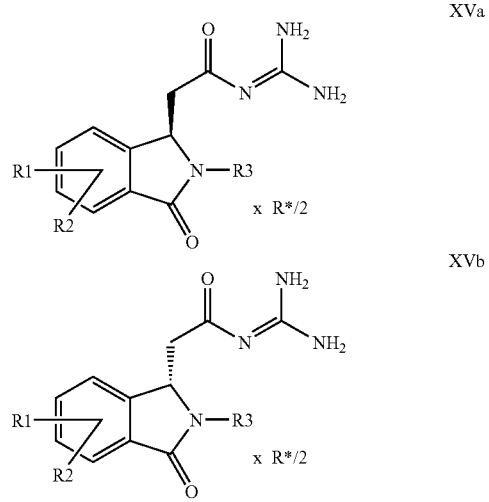

where
R1 and R2
  are each independently hydrogen, F, Cl, trifluoromethoxy, 2,2,2-trifluoroethoxy, trifluoromethyl, 2,2,2-trifluoroethyl or alkyl having 1, 2, 3 or 4 carbon atoms;
R3 is Alk-R4, trifluoromethyl;
  Alk is alkyl having 1, 2, 3 or 4 carbon atoms;
  R4 is hydrogen, trifluoromethyl or cycloalkyl having 3, 4, 5, 6 or 7 carbon atoms;
R* is

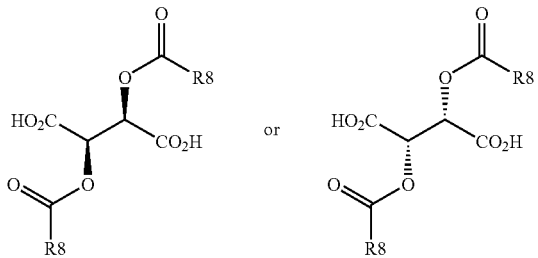

R8 is alkyl having 1, 2, 3, 4, 5 or 6 carbon atoms or phenyl which is unsubstituted or substituted by 1, 2 or 3 substituents from the group of F, Cl, Br, I, alkyl having 1, 2, 3 or 4 carbon atoms or alkoxy having 1, 2, 3 or 4 carbon atoms.

When the above-described compounds, for example the compounds of the formulae I, Ia, Ib, VII, XIII, XIV, XVa or XVb, contain one or more centers of asymmetry, they may each independently have either S or R configuration, unless stated otherwise. The compounds may be present in the form of optical isomers, of diastereomers, of racemates or of mixtures thereof, unless they are more precisely defined. On double bonds, either E or Z configuration may be present, unless stated otherwise. The present invention encompasses all tautomeric forms of the above-described compounds, for example of the compounds of the formulae I, Ia, Ib, XVa and XVb.

Alkyl radicals may be straight-chain or branched. This is also true when they bear substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. Preferred alkyl radicals are methyl, ethyl, n-propyl and isopropyl, more preferably methyl or ethyl. In alkyl radicals, one or more, for example 1, 2, 3, 4 or 5, hydrogen atoms may be substituted by fluorine atoms. Examples of such fluoroalkyl radicals are trifluoromethyl, 2,2,2-trifluoroethyl and pentafluoroethyl, preferably trifluoromethyl or 2,2,2-trifluoroethyl. Substituted alkyl radicals may be substituted in any positions.

Examples of cycloalkyl radicals are cyclopropyl, cyclobutyl, cyclopentyl, cyclohexyl or cycloheptyl.

Phenyl radicals may be unsubstituted or mono- or polysubstituted, for example mono-, di- or trisubstituted, by identical or different radicals. When a phenyl radical is substituted, it preferably bears one or two identical or different substituents. In monosubstituted phenyl radicals, the substituent may be be disposed in the 2-position, the 3-position or the 4-position. Disubstituted phenyl may be substituted in the 2,3-position, 2,4-position, 2,5-position, 2,6-position, 3,4-position or 3,5-position. In trisubstituted phenyl radicals, the substituents may be disposed in the 2,3,4-position, 2,3,5-position, 2,4,5-position, 2,4,6-position, 2,3,6-position or 3,4,5-position.

The above-described compounds, for example the compounds of the formulae I, Ia and Ib, may be used in the process according to the invention in the form of their salts and/or isolated in the form of their salts. Salts may be obtained by the customary methods, for example by reacting with acids or bases in a solvent, or by anion exchange or cation exchange from other salts. Useful acid addition salts, for example of the compounds of the formulae I, Ia and Ib, are, for example, halides, in particular hydrochlorides, hydrobromides, lactates, sulfates, citrates, tartrates, acetates, phosphates, methylsulfonates, benzenesulfonates, p-toluenesulfonates, adipates, fumarates, gluconates, glutamates, glycerolphosphates, maleates, benzoates, oxalates and pamoates and trifluoroacetates. In the case of the preparation of active ingredients, preference is given to physiologically tolerated salts and pharmaceutically acceptable salts. Examples include salts of compounds of the formulae I, Ia and Ib with fumaric acid, in particular salts which contain 1 mole of fumaric acid per mole of the compound of the formula I, Ia or Ib, and are thus hydrogenfumarates or hemifumarates. Advantageous properties such as crystallinity, stability, particularly low hygroscopicity, a low tendency to racemization and good solubility are features especially, for example, of (S)—N-{2-[3-oxo-2-(2,2,2-trifluoroethyl)-6-trifluoromethyl-2,3-dihydro-1H-isoindol-1-yl]acetyl}guanidine hydrogenfumarate hydrate of the formula XVI which likewise forms part of the subject matter of the present invention in all its tautomeric forms.

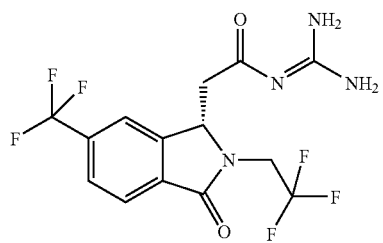

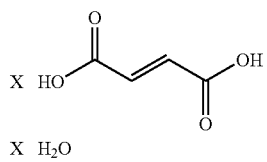

When the compounds contain an acid group, they may form salts with bases, for example alkali metal salts, preferably sodium salts or potassium salts, or ammonium salts, for example salts with ammonia or organic amines or amino acids. Compounds which contain a basic group and an acid group may also be present in the form of a zwitterion.

One embodiment of the present invention relates to compounds in which R1 and R2 are not both hydrogen, in particular to compounds in which R1 is hydrogen and R2 is fluorine, chlorine or trifluoromethyl, especially trifluoromethyl. In compounds in which R1 is hydrogen, the R2 substituent is preferably disposed in the para-position of the benzene ring relative to the C=O group in the isoindolone system.

The Alk group is preferably alkyl having 1, 2 or 3 carbon atoms, in particular having 1 or 2 carbon atoms, especially having 1 carbon atom. R4 is preferably trifluoromethyl or cycloalkyl having 3, 5 or 6 carbon atoms, in particular 3 carbon atoms, more preferably trifluoromethyl. One embodiment of the present invention relates to compounds in which R3 is trifluoromethyl or 2,2,2-trifluoroethyl, in particular 2,2,2-trifluoroethyl.

A special embodiment of the present invention relates to the preparation of N-{2-[3-oxo-2-(2,2,2-trifluoroethyl)-6-trifluoromethyl-2,3-dihydro-1H-isoindol-1-yl]acetyl}guanidine and its enantiomeric forms and salts thereof.

X is preferably chlorine or methoxy, in particular chlorine. R5 is preferably methoxy or ethoxy, in particular ethoxy. R6 is preferably methoxy or ethoxy, in particular ethoxy. R7 is preferably methoxy or ethoxy, in particular ethoxy.

In one embodiment of the present invention, R8 is phenyl which is unsubstituted or substituted by 1, 2 or 3 substitutents from the group of F, Cl, alkyl having 1, 2, 3 or 4 carbon atoms, or alkoxy having 1, 2, 3 or 4 carbon atoms, in particular unsubstituted phenyl.

The compounds of the formulae I, Ia, Ib, XVa and XVb and their pharmaceutically tolerated salts are substituted acylguanidines and inhibit the cellular sodium-proton antiporter ($Na^+/H^+$ exchanger, NHE), in particular the subtype NHE-1.

Owing to the NHE inhibitory properties, the compounds of the formulae I, Ia, Ib, XVa, XVb and XVI and/or their pharmaceutically acceptable salts are suitable for the prevention and treatment of disorders which are caused by activation of or by activated NHE, and also of disorders which have the NHE-related damage as a secondary cause. The compounds of the formulae I, Ia, Ib, Xva and XVb may also be used for the treatment and prevention of disorders in which the NHE is only partially inhibited, for example by using a lower dose.

Since NHE inhibitors act predominantly via their influence on cellular pH regulation, they can generally be advantageously combined with other compounds which regulate the intracellular pH value, useful combination partners being inhibitors of the enzyme group of the carbonic anhydrases, inhibitors of the systems transporting bicarbonate ions, such as of the sodium bicarbonate cotransporter (NBC) or of the sodium-dependent chloride-bicarbonate exchanger (NCBE), and also NHE inhibitors with inhibitory action on other NHE subtypes, because they can reinforce or modulate the pharmacologically relevant pH-regulating effects of the NHE inhibitors described here.

The use of the compounds of the formulae I, Ia, Ib, XVa, XVb or XVI relates to the prevention and the treatment of acute and chronic disorders in veterinary and in human medicine. For instance, the inventive inhibitors of the NHE are suitable for treating disorders that are caused by ischemia and by reperfusion.

As a result of their pharmacological properties, the compounds described here are suitable as antiarrhythmic medicaments. Their cardioprotective component makes NHE inhibitors outstandingly suitable for infarction prophylaxis and infarction treatment, and also for the treatment of angina pectoris, in which cases they also preventively inhibit or greatly reduce the pathophysiological processes when ischemia-induced damage arises, in particular when ischemia-induced cardiac arrhythmias are triggered. Owing to their protective actions against pathological hypoxic and ischemic situations, the compounds of the formulae I, Ia, Ib, XVa, XVb and XVI used in accordance with the invention and/or pharmaceutically acceptable salts thereof, as a result of inhibition of the cellular $Na^+/H^+$ exchange mechanism, may be used as medicaments for the treatment of all acute or chronic damage induced by ischemia or disorders induced primarily or secondarily thereby.

This also relates to their use as medicaments for surgical interventions. Thus, the compounds may be used in organ transplants, in which case the compounds may be used for the protection of the organs in the donor before and during the removal, to protect removed organs, for example in the course of treatment with or their storage in physiological bath liquids, and also in the course of transfer to the recipient organism.

The inventive compounds are likewise valuable medicaments having a protective action in the performance of angioplastic surgical interventions, for example on the heart and also on peripheral organs and vessels.

The inventive compounds may also be used when performing bypass operations, for example in bypass operations on coronary vessels and in Coronary Artery Bypass Graft (CABG).

Depending on their action against ischemia-induced damage, the inventive compounds of the formula I can even be used for resuscitation after a cardiac arrest.

The inventive compounds are of interest for medicaments against life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic action of medicaments like those finding use in particular in cancer therapy and the therapy of autoimmune diseases, combined administration with NHE inhibitors is suitable for inhibiting the cytotoxic, especially cardiotoxic, side effects of the compounds mentioned. The reduction in the cytotoxic effects, especially the cardiotoxicity, resulting from comedication with NHE1 inhibitors also makes it possible to increase the dose of the cytotoxic therapeutic agents and/or to prolong the medication with such medicaments. The therapeutic benefit of such a cytotoxic therapy can be considerably increased by the combination with NHE inhibitors.

Moreover, NHE1 inhibitors can be used in the event of heart-damaging overproduction of thyroid hormones, thyrotoxicosis, or when thyroid hormones are supplied externally. The compounds of the formulae I, Ia, Ib, XVa, XVb and XVI and/or the pharmaceutically acceptable salts thereof are thus suitable for improving therapy with cardiotoxic medicaments.

In accordance with their protective effect against ischemia-induced damage, the inventive compounds are also suitable as medicaments for the treatment of ischemias of the nervous system, especially of the central nervous system, and they are suitable, for example, for the treatment of stroke or of cerebral edema.

NHE inhibitors are also suitable for the therapy and prophylaxis of diseases and disorders which are induced by hyperexcitability of the central nervous system, in particular for the treatment of epileptic disorders, centrally induced clonic and tonic spasms, states of psychological depression, anxiety disorders and psychoses. In these cases, it is possible to use the NHE inhibitors described here alone or in combination with other substances having antiepileptic activity or antipsychotic active ingredients, or carbonic anhydrase inhibitors, for example with acetazolamide, and with other inhibitors of NHE or of the sodium-dependent chloride-bicarbonate exchanger (NCBE).

In addition, NHE inhibitors are likewise suitable for the treatment of types of shock, for example of allergic, cardiogenic, hypovolemic and bacterial shock.

The compounds of the formulae I, Ia, Ib, XVa, XVb and XVI and/or the pharmaceutically acceptable salts thereof may likewise be used for the prevention and treatment of thrombotic disorders, since they, as NHE inhibitors, are themselves also able to inhibit platelet aggregation. In addition, they are able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic action of significant thrombogenic factors. The NHE inhibitors of the present invention can therefore be combined with other anticoagulant and/or thrombolytic active ingredients, for example recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. It is particularly favorable to use the present NHE inhibitors in combination with NCBE inhibitors and/or with inhibitors of carbonic anhydrase, for example with acetazolamide.

In addition, NHE inhibitors feature a strong inhibitory effect on the proliferation of cells, for example fibroblast cell proliferation and the proliferation of smooth vascular muscle cells. The compounds of the formulae I, Ia, Ib, XVa, XVb and XVI and/or the pharmaceutically acceptable salts thereof are therefore useful as valuable therapeutic agents for diseases in which cellular proliferation represents a primary or secondary cause, and can therefore be used as antiatherosclerotics, agents for chronic renal failure, cancers.

It has been possible to show that cell migration is inhibited by NHE inhibitors. The compounds of the formulae I, Ia, Ib, XVa, XVb and XVI and/or the pharmaceutically acceptable salts thereof are therefore suitable as valuable therapeutic agents for diseases in which cell migration represents a primary or secondary cause, for example, cancers with a pronounced tendency to metastasis.

NHE inhibitors further feature a retardation or prevention of fibrotic disorders. They are thus suitable as excellent agents for the treatment of cardiac fibroses, and of pulmonary fibrosis, hepatic fibrosis, renal fibrosis and other fibrotic disorders.

They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of the formulae I, Ia, Ib, XVa, XVb and XVI and/or the pharmaceutically acceptable salts thereof are suitable for the prevention and treatment of high blood pressure and for the treatment of cardiovascular disorders. In these cases they can be used alone or with a suitable combination and formulation partner for the treatment of high blood pressure and of cardiovascular disorders. For example, one or more diuretics with a thiazide-like action, loop diuretics, aldosterone and pseudoaldosterone antagonists, such as hydrochlorothiazide, indapamide, polythiazide, furosemide, piretamide, torasemide, bumetamide, amiloride, triamterene, spironolactone or eplerone, may be combined. The NHE inhibitors of the present invention may also be used in combination with calcium antagonists such as verapamil, diltiazem, amlodipine or nifedipine, and with ACE inhibitors, for example ramipril, enalapril, lisinopril, fosinopril or captopril. Further favorable combination partners are also β-blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has been shown that NHE1 inhibitors have a significant antiinflammatory effect and can thus be used as antiinflammatory drugs. The inhibition of the release of mediators of inflammation is noteworthy in this connection. The compounds may thus be used alone or in combination with an antiinflammatory drug in the prevention or treatment of chronic and acute inflammatory disorders. The combination partners used advantageously are steroidal and non-steroidal antiinflammatory drugs. The inventive compounds may also be used for the prevention or treatment of diseases which are caused by protozoa, such as in the event of malaria or coccidiosis in poultry.

It has also been found that NHE inhibitors exhibit a beneficial effect on serum lipoproteins. It is generally acknowledged that blood fat levels which are too high, known as hyperlipoproteinemias, constitute an essential risk factor for the development of arteriosclerotic vascular lesions, especially coronary heart disease. The reduction of elevated serum lipoproteins is therefore of exceptional importance for the prophylaxis and the regression of atherosclerotic lesions. In addition to the reduction in total serum cholesterol, it is particularly important to reduce the proportion of specific atherogenic lipid fractions in this total cholesterol, in particular of the low density lipoproteins (LDL) and of the very low density lipoproteins (VLDL), since these lipid fractions constitute an atherogenic risk factor. By contrast, a protective function against coronary heart disease is ascribed to the high density lipoproteins. Accordingly, hypolipidemics should be capable of reducing not only total cholesterol but also in particular the VLDL and LDL serum cholesterol fractions. It has now been found that NHE1 inhibitors exhibit valuable therapeutically utilizable properties in relation to influencing the serum lipid levels. For instance, they significantly reduce the elevated serum concentrations of LDL and VLDL, as can be observed, for example, as a result of increased dietary intake of a cholesterol- and lipid-rich diet or in cases of pathological metabolic alterations, for example genetically related hyperlipidemias. They can therefore be used for the prophylaxis and for the regression of atherosclerotic lesions by eliminating a causal risk factor. These include not only the primary hyperlipidemias but also certain secondary hyperlipidemias, as occur, for example, in the event of diabetes. In addition, NHE inhibitors lead to a marked reduction in the infarctions induced by metabolic abnormalities and in particular to a significant reduction in the induced infarction size and the severity thereof.

The inventive compounds of the formulae I, Ia, Ib, XVa, XVb and XVI therefore advantageously find use for preparing a medicament for the treatment of hypercholesterolemia; for preparing a medicament for the prevention of atherogenesis; for preparing a medicament for the prevention and treatment of atherosclerosis, for preparing a medicament for the prevention and treatment of diseases which are induced by elevated cholesterol levels, for preparing a medicament for the prevention and treatment of diseases induced by endothelial dysfunction, for preparing a medicament for the prevention and treatment of atherosclerosis-induced hypertension, for preparing a medicament for the prevention and treatment of atherosclerosis-induced thromboses, for preparing a medicament for the prevention and treatment of hypercholesterolemia-induced and endothelial dysfunction-induced ischemic damage and post-ischemic reperfusion damage, for preparing a medicament for the prevention and treatment of hypercholesterolemia-induced and endothelial dysfunction-induced cardiac hypertrophies and cardiomyopathies and of congestive heart failure (CHF), for preparing a medicament for the prevention and treatment of hypercholesterolemia-induced and endothelial dysfunction-induced coronary vasospasms and myocardial infarctions, for preparing a medicament for the treatment of the disorders mentioned in combinations with hypotensive substances, preferably with angiotensin converting enzyme (ACE) inhibitors and angiotensin receptor antagonists. A combination of an NHE inhibitor with an active ingredient lowering the blood fat levels, preferably with an HMG-CoA reductase inhibitor (for example lovastatin or pravastatin), the latter bringing about hypolipidemic action and thus increasing the hypolipidemic properties of the NHE inhibitor, is found to be a favorable combination with enhanced action and reduced use of active ingredients.

For instance, NHE inhibitors lead to effective protection against endothelial damage of various origins. This protection of the vessels against the syndrome of endothelial dysfunction makes compounds of the formulae I, Ia, Ib, XVa, XVb and XVI and/or the pharmaceutically acceptable salts thereof valuable medicaments for the prevention and for the treatment of coronary vasospasms, peripheral vascular diseases, in particular intermittent claudication, atherogenesis and atherosclerosis, left ventricular hypertrophy and dilated cardiomyopathy and thrombotic disorders.

It has also been found that NHE inhibitors are suitable in the treatment of non-insulin-dependent diabetes (NIDDM), in the course of which the insulin resistance is restrained. In this case, it may be beneficial to enhance antidiabetic activity and quality of action of the inventive compounds by combining them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

In addition to the acute antidiabetic effects, NHE inhibitors counteract the development of late complications of diabetes and can therefore be used as medicaments for the prevention and treatment of late damage from diabetes, such as diabetic nephropathy, diabetic neuropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin might be particularly important in this connection.

NHE inhibitors exhibit, in addition to the protective effects against acute ischemic events and the subsequent equally acutely stressing reperfusion events, also direct therapeutically utilizable actions against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders which are connected with an age-related functional impairment or with age-related manifestations of wear on organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. NHE inhibitors are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart which is caused inter alia by deposition of connective tissue in the myocardial tissue. This deposition of connective tissue is characterized by an increase in the weight of the heart, by an enlargement of the heart and by restricted cardiac function. It is surprising that it has been possible to virtually completely inhibit such aging of the heart organ. NHE inhibitors are thus outstandingly suitable for the treatment and prevention of heart failure, of congestive heart failure (CHF).

Inhibition of proliferation allows not only forms of cancer which have already occurred to be cured, but also reduction and highly significant retardation of the age-related incidence of cancer through NHE inhibitors. A particularly noteworthy finding is that the disorders, occurring as a result of aging, of all organs and not only certain types of cancer are suppressed or occur with a highly significant delay. NHE inhibitors are thus outstandingly suitable for the treatment and, in particular, the prevention of age-related types of cancer.

Using NHE inhibitors, a delay, shifted highly significantly in time, is found in the occurrence of age-related disorders of all the organs investigated, including the heart, vessels, liver etc., and also a highly significant delay in cancer of the elderly. Moreover, there is also surprisingly a prolongation of life to an extent which has to date been achievable by no other group of medicaments or by any natural products. This unique effect of NHE inhibitors also enables, in addition to the sole use of the active ingredients on humans and animals, these NHE inhibitors to be combined with other activity principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, it is possible to combine with dietary measures, for example with appetite suppressants. It is equally possible to consider a combination with hypotensive medicaments such as with ACE inhibitors, angiotensin receptor antagonists, diuretics, $Ca^{2+}$ antagonists etc. or with metabolism-normalizing medicaments such as cholesterol-lowering agents.

NHE inhibitors are thus outstandingly suitable for the prevention of age-related tissue changes and for prolonging life while retaining a high quality of life.

The inventive compounds are effective inhibitors of the cellular sodium-proton antiporter (Na/H exchanger) which in numerous disorders (essential hypertension, atherosclerosis, diabetes etc.) is also increased in cells which are readily amenable to measurements, for example in erythrocytes, thrombocytes or leukocytes. The compounds used in accordance with the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

Also claimed is a medicine for human, veterinary or phytoprotective use which, together with pharmaceutically acceptable carriers and excipients, comprises an effective amount of one or more compounds of the formulae XVa, XVb and XVI and/or pharmaceutically acceptable salts thereof, alone or in combination with other pharmacological active ingredients or medicaments. Medicaments which comprise a compound of the formulae I, Ia, Ib, XVa, XVb and XVI and/or the pharmaceutically acceptable salts thereof can be administered, for example, orally, parenterally, intravenously, rectally, percutaneously or by inhalation, the preferred administration being dependent on the particular characteristics of the disorder. The compounds of the formulae I, Ia, Ib, XVa, XVb and XVI may be used alone or together with pharmaceutical excipients, both in veterinary medicine and in human medicine. The medicaments generally comprise active ingredients of the formulae I, Ia, Ib, XVa, XVb and XVI and/or the pharmaceutically acceptable salts thereof in an amount of from 0.01 mg to 1 g per dose unit.

Which excipients are suitable for the desired pharmaceutical formulation are familiar to those skilled in the art on the basis of their expert knowledge. In addition to solvents, gel formers, suppository bases, tablet excipients, and other active ingredient carriers, it is possible to use, for example, antioxidants, dispersants, emulsifiers, antifoams, flavorings, preservatives, solubilizers or colors.

For an oral administration form, the active compounds are mixed with additives suitable therefor, such as carriers, stabilizers or inert diluents, and converted by conventional methods to suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. The formulation may be effected either in the form of a dry granule or a wet granule. Examples of suitable oily carriers or solvents are vegetable or animal oils such as sunflower oil or fish liver oil.

For subcutaneous, intramuscular or intravenous administration, the active compounds used, if desired with the substances customary therefor, such as solubilizers, emulsifiers or other excipients, are brought into solution, suspension or emulsion. Examples of useful solvents are: water, physiological saline or alcohols, e.g. ethanol, propanol, glycerol, as well as sugar solutions such as glucose or mannitol solutions, or else a mixture of the different solvents mentioned.

Suitable pharmaceutical formulations for administration in the form of aerosols or sprays are, for example, solutions, suspensions or emulsions of the active ingredient of the formulae I, Ia, Ib, XVa, XVb and XVI and/or the pharmaceutically acceptable salts thereof in a pharmaceutically acceptable solvent, in particular ethanol or water, or a mixture of such solvents. The formulation may, if required, also contain other pharmaceutical excipients such as surfactants, emulsifiers and stabilizers, and a propellant gas. Such a formulation normally contains the active ingredient in a concentration of about 0.1 to 10%, in particular of about 0.3 to 3% by weight.

The dose of the active ingredient of the formulae I, Ia, Ib, XVa, XVb and XVI to be administered, and the frequency of administration, depend upon the potency and duration of action of the compounds used; additionally also on the nature and severity of the disorder to be treated and on the sex, age, weight and individual responsiveness of the mammal to be treated.

On average, the daily dose of a compound of the formulae I, Ia, Ib, XVa, XVb and XVI and/or the pharmaceutically acceptable salts thereof for a patient weighing about 75 kg is at least 0.001 mg/kg, preferably 0.01 mg/kg, up to at most 10 mg/kg, preferably 1 mg/kg, of body weight. In the event of acute episodes of the disorder, for example immediately after suffering a myocardial infarction, higher and especially more frequent dosages may also be necessary, for example up to 4 single doses a day. Especially in the case of i.v. administration, for instance for a patient with infarction in the intensive care unit, for example up to 700 mg per day may be necessary, and the inventive compounds may be administered by infusion.

LIST OF ABBREVIATIONS

DCC dicyclohexyl carbodiimide
DIP diisopropyl ether
TLC thin-layer chromatography
DMF N,N-dimethylformamide
EA ethyl acetate
eq. equivalent
Et$_3$N triethylamine
Et$_2$O diethyl ether
EtOH ethanol
h hour(s)
HEP n-heptane
HOAc acetic acid
KOtBu potassium 2-methyl-2-propoxide
MeOH methanol
min minute(s)
mp melting point
MTB tert-butyl methyl ether
NMP 1-methylpyrrolidin-2-one
Pd(OAc)$_2$ palladium(II) acetate
RT room temperature
rt retention time
tBu tert-butyl THF tetrahydrofuran
TMEDA N,N,N',N'-tetramethylethane-1,2-diamine The retention times (rt) reported hereinbelow relate to HPLC analyses having the following parameters:

Method A:
Stationary phase: Waters Symmetry C8 (5μ) 3.9×150 mm
Mobile Phase: isocratic CH$_3$CN/0.1% aqueous CF$_3$CO$_2$H 35:65; λ=220 nm; 1 ml/min.

Method B:
Stationary phase: Waters Symmetry C8 (5μ) 3.9×150 mm
Mobile Phase: isocratic CH$_3$CN/0.1% aqueous CF$_3$CO$_2$H 40:60; λ=230 nm; 1 ml/min.

Method C:
Stationary phase: Waters Symmetry C8 (5μ) 3.9×150 mm
Mobile Phase: isocratic CH$_3$CN/0.1% aqueous CF$_3$CO$_2$H 50:50; λ=220 nm; 1 ml/min.

EXAMPLE 1 a) N-(2,2,2-Trifluoroethyl)-4-trifluoromethylbenzamide

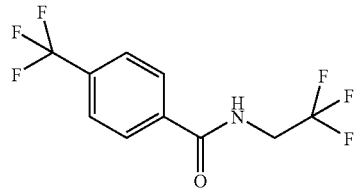

5.0 g (24 mmol) of 4-trifluoromethylbenzoyl chloride and 5.0 ml (36 mmol) of triethylamine were dissolved in 50 ml of CH$_2$Cl$_2$ and 2.4 g (24 mmol) of 2,2,2-trifluoroethylamine were slowly added dropwise at RT. The mixture was stirred at RT for 4 h, then the volatile constituents were removed under reduced pressure. The residue was taken up using 100 ml of MTB and washed initially with 30 ml of a saturated aqueous Na$_2$CO$_3$ solution and then with 30 ml of a saturated aqueous NaHSO$_4$ solution. Drying was effected over MgSO$_4$ and 6.1 g (94%) of a colorless resin were obtained which crystallized when left to stand; mp: 117° C.

R$_f$(DIP)=0.50 MS (EI): 271 (M+1)$^+$ b) (R,S)-3-Hydroxy-2-(2,2,2-trifluoroethyl)-5-trifluoromethyl-2,3-dihydroisoindol-1-one

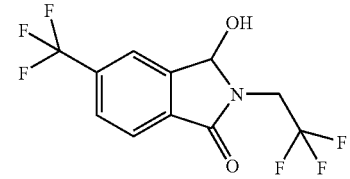

0.37 ml (2.4 mmol) of TMEDA and 1.4 ml (2.3 mmol) of a 1.5 M solution of t-BuLi in n-pentane were dissolved at −75° C. in 2 ml of THF (anhydrous) and a solution of 0.30 g (1.1 mmol) of N-(2,2,2-trifluoroethyl)-4-trifluoromethylbenzamide in 2 ml of THF was added dropwise at −75° C. The mixture was stirred at −75° C. for 3 h, then 0.43 ml (5.5 mmol)

of DMF was added dropwise and the mixture was warmed to RT over 30 minutes. The reaction mixture was poured onto 100 ml of a saturated aqueous NaHCO$_3$ solution and extracted 3 times with 30 ml each time of EA. Drying was effected over MgSO$_4$ and the solvent was removed under reduced pressure. Chromatography on silica gel using DIP afforded 80 mg of (R,S)-3-hydroxy-2-(2,2,2-trifluoroethyl)-5-trifluoromethyl-2,3-dihydroisoindol-1-one in addition to 110 mg of mixture with starting material. This mixture was separated again by reversed phase HPLC (conditions see below) and a further 40 mg of (R,S)-3-Hydroxy-2-(2,2,2-trifluoroethyl)-5-trifluoromethyl-2,3-dihydroisoindol-1-one were obtained; overall yield 30%.

HPLC: gradient, run time 20 min

Eluent: 0.1% aqueous CF$_3$CO$_2$H, acetonitrile (Chromasolv); flow rate: 30 ml/min Column: Waters Xterra™ MS C18 5 μm, 30×100 mm Gradient:

| | |
|---|---|
| 0–2.5 min | 10% acetonitrile |
| 3.0 min | 25% acetonitrile |
| 14.0 min | 75% acetonitrile |
| 15.0 min | 95% acetonitrile |
| 17.5 min | 10% acetonitrile |

R$_f$ (DIP)=0.50 MS (EI): 299 (M+1)$^+$ c) Ethyl (RS)-[3-oxo-2-(2,2,2-trifluoroethyl)-6-trifluoromethyl-2,3-dihydro-1H-isoindol-1-yl]acetate

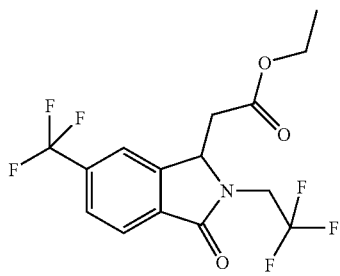

Under argon, ethyl. (diethoxyphosphoryl)acetate (135 mg, 0.6 mmol) was dissolved in anhydrous dimethoxyethane (10 ml). 17.6 mg of NaH (60% in oil) were added at RT to this solution which was stirred at RT for 10 min. Afterward, a solution of 120 mg (0.04 mmol) of (RS)-3-hydroxy-2-(2,2,2-trifluoroethyl)-5-trifluoromethyl-2,3-dihydroisoindol-1-one in anhydrous dimethoxyethane (5 ml) was added and the mixture was subsequently stirred at reflux for 2 h. The reaction solution was left to cool; the reaction solution was then poured onto 50 ml of 5% sodium hydrogencarbonate solution and extracted twice with 20 ml each time of ethyl acetate; the organic phase was dried over MgSO$_4$ and concentrated under reduced pressure, and the residue was purified by chromatography on silica gel using DIP as the eluent. 90 mg (61%) of ethyl (RS)-[3-oxo-2-(2,2,2-trifluoroethyl)-6-trifluoromethyl-2,3-dihydro-1H-isoindol-1-yl]acetate were obtained as a colorless oil which crystallized from heptane as a beige solid.

Rf (DIP)=0.31

The NMR spectrum was identical to the material prepared in example 4.

d) (R,S)-N-{2-[3-Oxo-2-(2,2,2-trifluoroethyl)-6-trifluoromethyl-2,3-dihydro-H-isoindol-1-yl] acetyl}guanidine

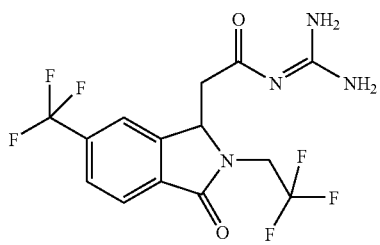

As described in example 2g), ethyl (RS)-[3-oxo-2-(2,2,2-trifluoroethyl)-6-trifluoromethyl-2,3-dihydro-1H-isoindol-1-yl]acetate may be reacted with guanidine.

EXAMPLE 2 a) 2-Nitro-4-trifluoromethylbenzoic acid

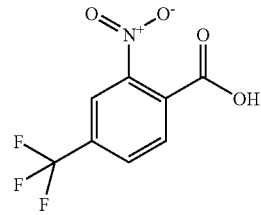

11.97 g of 4 trifluoromethylbenzoic acid (63 mmol) were added slowly in portions at RT to 48 ml of HNO$_3$ (100%). The mixture was subsequently heated to reflux for 1 h, then cooled to RT and poured onto about 600 g of ice. The mixture was stirred for 1 h, then the precipitate was filtered off and washed with 1 l of water. The filtrate was extracted with 300 ml of CH$_2$Cl$_2$, and the organic phase was combined with the precipitate and dried over Na$_2$SO$_4$. The solvent was removed under reduced pressure and the residue was recrystallized by dissolving in 1 l of DIP at 68° C., adding 2 l of HEP at this temperature and finally cooling the solution slowly to RT. The crystallized product was washed with 1 l of HEP and dried under reduced pressure to obtain 7.1 g (48%), mp 136° C.-138° C.

b) 2-Amino-4-trifluoromethylbenzoic acid

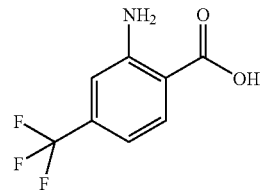

250 g of 2-nitro-4-trifluoromethylbenzoic acid (1.06 mol) were dissolved in 1 l of EtOH and 7.5 g of Pd/C (5%) were added. The mixture was hydrogenated under 1-2.5 bar of hydrogen pressure. During the hydrogen uptake, the temperature rose temporarily from 10° C. to 104° C. After 2 h, the hydrogen uptake was complete. Subsequently, the catalyst was filtered off and the solvent was removed under reduced pressure to obtain 215 g (99%) of a pale yellow solid, mp 174-176° C.

c) 2-((E)-2-Ethoxycarbonylvinyl)-4-trifluoromethyl-benzoic acid

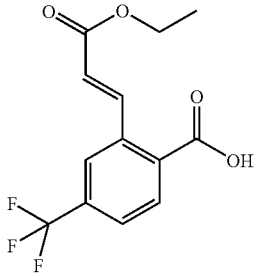

520 mg of NaNO$_2$ (7.6 mmol) were dissolved in 2 ml of water and added dropwise at 0° C. to a solution of 1.3 g of 2-amino-4-trifluoromethylbenzoic acid (6.5 mmol) in 2.6 ml of a 48% aqueous HBF$_4$ solution and 30 ml of ethanol. The mixture was then stirred at 0° C. for 10 minutes, then warmed to RT. A further 0.3 ml of a 48% aqueous HBF$_4$ solution was then added, then 30 ml of ethanol, 0.9 g of ethyl acrylate (9.0 mmol) and 26.9 mg of Pd (OAc)$_2$ (0.12 mmol). Subsequently, the mixture was stirred at 50-60° C. for 1 h. The solvent was then removed under reduced pressure, and the residue taken up with 25 ml of EA and washed initially with 25 ml of a 1N aqueous HCl solution then with 25 ml of a saturated aqueous NaCl solution. The organic phase was dried over Na$_2$SO$_4$ and the solvent removed under reduced pressure. The residue was suspended in 25 ml of heptane and the precipitated product was filtered off. Yield: 1.3 g (69%) of a pale brownish solid. An analytical sample was purified by crystallization from heptane/ethyl acetate.

The NMR spectrum was identical to the material prepared in example 3a.

d) Ethyl (E)-3-[2-(2,2,2-trifluoroethylcarbamoyl)-5-trifluoromethylphenyl]acrylate

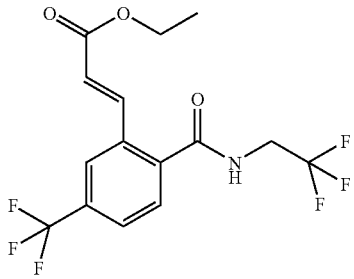

1.3 g of 2-(2-ethoxycarbonylvinyl)-4-trifluoromethylbenzoic acid (4.5 mmol) and 453 mg of 2,2,2-trifluoroethylamine (4.5 mmol) were dissolved in 5 ml of DMF and 0.93 g of DCC was added. The mixture was stirred at RT for 4 h. The urea by-product was removed by filtration and then the solvent was removed under reduced pressure. The residue was recrystallized from DIP to obtain 1.6 g (96%) of white crystals.

The NMR spectrum was identical to the material prepared in example 3b.

e) (RS)-[3-Oxo-2-(2,2,2-trifluoroethyl)-6-trifluoromethyl-2,3-dihydro-1H-isoindol-1-yl]acetic acid

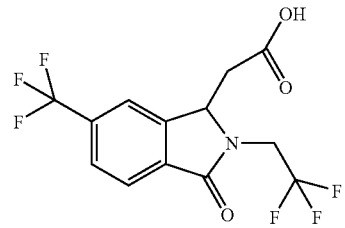

2.2 g of ethyl (E)-3-[2-(2,2,2-trifluoroethylcarbamoyl)-5-trifluoromethylphenyl]acrylate (5.9 mmol) were dissolved in 10 ml of methanol and 1.5 ml of a 5 M aqueous NaOH solution (7.5 mmol) were added. The mixture was stirred at RT for 18 h and then set to pH=7 using aqueous HCl solution. The solvents were removed under reduced pressure and the residue was suspended in 10 ml of water. This suspension was set to pH=2 using a 2N aqueous HCl solution and extracted 3 times with 10 ml each time of EA. Drying was effected over Na$_2$SO$_4$ and the solvent was removed under reduced pressure. The residue was crystallized with diethyl ether/DIP, mp: 202-204° C.

Yield: 1.8 g (89%). $^1$H NMR (400 MHz, CDCl$_3$): δ=3.07 (dd, J$_1$=17 Hz, J$_2$=6 Hz, 1 H), 3.23 (dd, J$_1$=17 Hz, J$_2$=5 Hz, 1 H), 4.27 (m, 1 H), 4.58 (m, 1 H), 5.08 (t, J=5 Hz, 1 H), 7.91 (d, J=8 Hz, 1 H), 7.96 (d, J=8 Hz, 1 H), 8.12 (s, 1 H), 12.50 (bs, 1 H) ppm.

Combustion analysis: C$_{13}$H$_9$F$_6$NO$_3$ (341.2): calc. C, 45.76; H, 2.66; N, 4.10. found C, 45.71; H, 2.43; N, 4.11.

f) Ethyl (RS)-[3-oxo-2-(2,2,2-trifluoroethyl)-6-trifluoromethyl-2,3-dihydro-1H-isoindol-1-yl]acetate

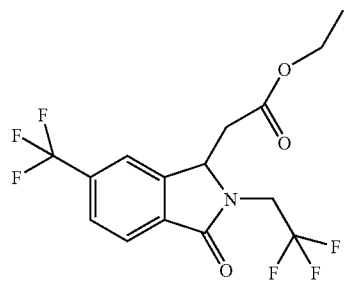

2.6 ml of SOCl$_2$ (35 mmol) were dissolved in 20 ml of ethanol and 3.4 g of (R,S)-[3-oxo-2-(2,2,2-trifluoroethyl)-6-trifluoromethyl-2,3-dihydro-1H-isoindol-1-yl]acetic acid (10 mmol) were added at −10° C. The mixture was stirred at RT for 18 h and the volatile constituents were subsequently removed under reduced pressure. The residue was chromatographed on silica gel using 3:1 HEP/EA. Yield: 3.0 g (81%) of a colorless oil which crystallized from heptane as a beige solid.

The NMR spectrum was identical to the material prepared in example 4.

g) (RS)-N-{-[3-Oxo-2-(2,2,2-trifluoroethyl)-6-trifluoromethyl-2,3-dihydro-H-isoindol-1-yl]acetyl}guanidine

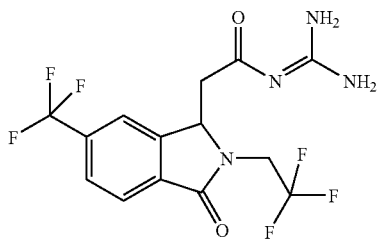

Guanidine hydrochloride (11.5 g, 120 mmol) was dissolved in NMP (45 ml) and KOtBu (11.2 g, 100 mmol) was added with stirring, and the mixture was left to stir at RT for 1.5 h and filtered. The filtrate was added dropwise at RT with stirring to a solution of ethyl (RS)-[3-oxo-2-(2,2,2-trifluoroethyl)-6-trifluoromethyl-2,3-dihydro-1H-isoindol-1-yl]acetate (7.38 g, 20 mmol) in NMP (12 ml) and left to stir at RT for a further 60 min. Subsequently, ice-water (270 ml) was added, the mixture was set to pH 7 using 2N HCl, ethyl acetate (60 ml) was added and the pH was subsequently adjusted to 8-8.5 by adding NaHCO$_3$ solution. The mixture was stirred vigorously at RT for 1 h and the precipitate formed was filtered off with suction and washed with water. 7.06 g (83%) of (R,S)-N-{2-[3-oxo-2-(2,2,2-trifluoroethyl)-6-trifluoromethyl-2,3-dihydro-H-isoindol-1-yl]acetyl}guanidine, inclusion compound with 0.5 equivalent of ethyl acetate, were obtained as light yellow crystals, mp. 160-161° C. with gradual heating, escape of ethyl acetate from approximately 90° C.

Rf (ethyl acetate/methanol)=0.45 $^1$H NMR (400 MHz, CDCl$_3$): δ=2.54 (dd, J$_1$=8 Hz, J$_2$=16 Hz, 1 H), 3.09 (dd, J$_1$=4 Hz, J$_2$=16 Hz, 1 H), 4.25 (m, 1 H), 4.64 (m, 1 H), 5.18 (m, 1 H), 6.65 (bs, 2 H), 7.75 (bs, 2 H), 7.88 (d, J=8 Hz, 1 H), 7.95 (d, J=8 Hz, 1 H), 8.02 (s, 1 H) ppm. C$_{14}$H$_{12}$F$_6$N$_4$O$_2$·½C$_4$H$_8$O$_2$ (426.33): calc. C, 45.08; H, 3.78; N, 13.14. found C, 45.07; H, 3.79; N, 13.01.

EXAMPLE 3 a) 2-((E)-2-Ethoxycarbonylvinyl)-4-trifluoromethylbenzoic acid (Variant of Example 2c)

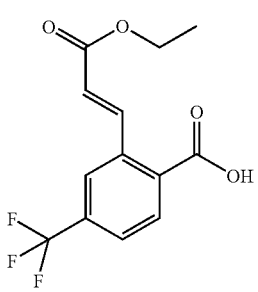

658 ml of a 48-50% aqueous HBF$_4$ solution were added at RT to 339 g of 2-amino-4-trifluoromethylbenzoic acid (1.65 mol) in 6.8 l of EtOH (anhydrous). The temperature rose from 21° C. to 26° C. The mixture was then cooled to 0° C. and a solution of 125 g of NaNO$_2$ in 500 ml of water was added dropwise between 0° C. and 5° C. over 17 minutes. The initially pale yellow solution became initially an orange-red suspension and finally a light yellow suspension. The progress of the reaction was monitored by HPLC (method B; 2-amino-4-trifluoromethylbenzoic acid rt=6.4 min; 2-carboxy-5-trifluoromethylbenzenediazonium salt intermediate=1.1 min. Within 30 minutes, the conversion to the 2-carboxy-5-trifluoromethylbenzenediazonium salt was >99% complete. The mixture was then added to 231 g of ethyl acrylate (2.31 mol), 11.1 g of Pd(OAc)$_2$ (49 mmol) and 6.8 l of ethanol (anhydrous) and the reaction mixture was heated to 49-51° C. A uniform evolution of nitrogen increasing with increasing temperature was observed. The reaction was monitored by HPLC (method B; 2-((E)-2-ethoxycarbonylvinyl)-4-trifluoromethylbenzoic acid rt=16.4 min). After 45 min, the degree of conversion was above 99%. The mixture was then cooled to RT and the solvent removed under reduced pressure. The residue was taken up in 3 l of EA and filtered off. The filtrate was then washed initially 3 times with 2.1 l each time of an aqueous HCl solution, then with 1 l of a saturated aqueous NaCl solution. Drying was effected over Na$_2$SO$_4$ and the solvent was removed under reduced pressure to obtain 449 g of a light brown solid. Taking into account an impurity (4-trifluoromethylbenzoic acid; 6.3%) and solvent residues (EA; 4%), a yield of 83% was obtained. An analytical sample was purified by crystallization from heptane/ethyl acetate. Mp.: 132-133° C. $^1$H NMR (400 MHz, CDCl$_3$): δ=1.36 (t, J=7 Hz, 3 H), 4.31 (q, J=7 Hz, 2 H), 6.41 (d, J=16 Hz, 1 H), 7.72 (d, J=8 Hz, 1 H), 7.86 (s, 1 H), 8.21 (d, J=8 Hz, 1 H), 8.51 (d, J 8.5-9.5 (bs, 1 H) ppm. Combustion analysis: C$_{13}$H$_{11}$F$_3$O$_4$ (288.23): calc. C, 54.17; H, 3.85. found C, 54.24; H, 3.74.

b) Ethyl (E)-3-[2-(2,2,2-trifluoroethylcarbamoyl)-5-trifluoromethylphenyl]acrylate

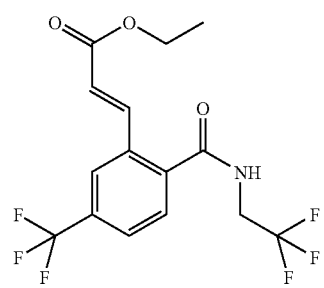

315 g of oxalyl chloride (2.48 mol) were added at a temperature between 15 and 18° C. over 24 min to a mixture of 650 g of 2-((E)-2-ethoxycarbonylvinyl)-4-trifluoromethylbenzoic acid (2.25 mol), 33 ml of DMF and 7.8 l of CH$_2$Cl$_2$. During the addition, gas evolution was observed. The mixture was stirred at RT for 1 h and then cooled to 5° C., and 285 g of Et$_3$N (2.81 mol) was then added at a temperature between 5° C. and 10° C. over a period of 27 min.

The mixture was stirred at 5° C. for a further 10 min, then 279 g of 2,2,2-trifluoroethylamine (2.81 mol) were added at a temperature between 9° C. and 20° C. over a period of 27 min. The mixture was stirred at RT for 10 ml, in the course of which a thick precipitate precipitated out, and, to improve the stirrability of the mixture, an additional 1 l of CH$_2$Cl$_2$ was added. The reaction was monitored by HPLC (method C; 2-((E)-2-ethoxycarbonylvinyl)-4-trifluoromethylbenzoic acid rt=5.9 min; ethyl (E)-3-[2-(2,2,2-trifluoroethylcarbamoyl)-5-trifluoromethylphenyl]acrylate rt=13.2 min). After stirring at RT for a further 50 min, the reaction was complete. Volatile constituents of the reaction mixture were then removed under reduced pressure, and the residue was taken up with 12 l of EA and washed 3 times with 2.5 l each time of water, then twice with 2.5 l each time of a saturated aqueous NaHCO$_3$ solution and finally with 1.5 l of a saturated aqueous NaCl solution. Drying was effected over MgSO$_4$, and the solvent was removed under reduced pressure to obtain 802 g of ethyl (E)-3-[2-(2,2,2-trifluoroethylcarbamoyl)-5-trifluoromethylphenyl]acrylate as a brown solid. This crude substance was combined with the crude product of another batch (177 g) and dissolved at 60-70° C. in 3 l of EA, and 14 l of HEP were added at this temperature in 1 l portions. The mixture was then heated to 80° C. and stirred at this temperature for 1.5 h. This mixture was then added to 5.6 l of HEP at 70° C. and the mixture was then cooled to RT with stirring over a period of 5 h. The product was then filtered off, washed with 3 l of HEP and dried under air to obtain 689 g of ethyl (E)-3-[2-(2,2,2-trifluoroethylcarbamoyl)-5-trifluoromethylphenyl]acrylate (67%) as a light brown solid. Mp: 161.5-162° C.

$^1$H NMR (400 MHz, CDCl$_3$): δ=1.33 (t, J=7 Hz, 3 H), 4.05 (m, 2 H), 4.26 (q, J=7 Hz, 2 H), 6.19 (bs, 1 H), 6.46 (d, J=16 Hz, 1 H), 7.63 (d, J=8 Hz, 1 H), 7.68 (d, J=8 Hz, 1 H), 7.87 (s, 1 H), 7.90 (d, J=16 Hz, 1 H) ppm. Combustion analysis: C$_{15}$H$_{13}$F$_6$NO$_3$ (369.27):calc. C, 48.79; H, 3.55; N, 3.79. found C, 48.93; H, 3.51; N, 3.92.

c) (R,S)-N-{2-[3-Oxo-2-(2,2,2-trifluoroethyl)-6-trifluoromethyl-2,3-dihydro-H-isoindol-1-yl]acetyl}guanidine

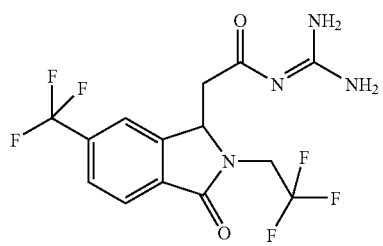

386 g of ethyl (E)-3-[2-(2,2,2-trifluoroethylcarbamoyl)-5-trifluoromethylphenyl]acrylate (1.05 mol) was suspended in 600 ml of DMF and added at a temperature between 5° C. and 15° C. in portions slowly to 4.7 g of KOtBu (42 mmol). The cyclization to the isoindolone was monitored by TLC (HEP/EA=2:1; ethyl acrylate: R$_f$=0.32; isoindolone: R$_f$=0.41). After one hour, the reaction was complete. In the meantime, 587 g of KOtBu were suspended in 2.2 l of DMF and 600 g of guanidinium chloride were added at a temperature of between 20° C. and 25° C. The mixture was stirred at 25° C. for 1 h and then the KCl was filtered off. The filtrate comprising the released guanidine was then added to the reaction mixture comprising the isoindolone and stirred at RT for 2 h. The conversion to the acylguanidine was monitored via HPLC (method b; wavelength 230 nm and 254 nm; isoindolone: rt=15.1 min; acylguanidine: rt=2.9 min). Subsequently, the reaction mixture was poured onto 14 l of ice-water, set to pH 8.5-9.0 using aqueous HCL solution and extracted 4 times with 3 l each time of EA. The mixture was then washed 3 times with 3 l each time of a saturated aqueous NaCl solution and dried over Na$_2$SO$_4$, and the solvent was removed under reduced pressure. 329 g (82%) of a brown solid were obtained. The product was combined with 3 other batches of the same preparation process; total amount 842 g. These 842 g (2.2 mol) were digested in 2 l of EA and 5 l of Et$_2$O at 30° C. for 2 h. The solid was then filtered off, washed twice with 2 l each time with Et$_2$O and dried under reduced pressure. 693 g (82% recovery) of an almost white solid were obtained. The compound crystallized from 2-propanol as the inclusion compound with 0.5 equivalent of 2-propanol.

The NMR spectrum was identical to the S-enantiomer prepared in example 5b.

EXAMPLE 4

Ethyl (RS)-(2-(2,2,2-trifluoroethyl)-3-oxo-6-trifluoromethyl-2,3-dihydro-1H-isoindol-1-yl)acetate by One-Pot Reaction Starting from 2-((E)-2-ethoxycarbonylvinyl)-4-trifluoromethylbenzoic acid

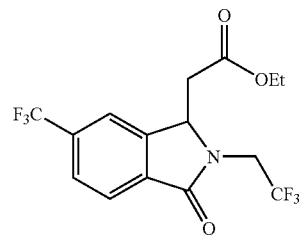

SOCl$_2$ (1.98 g, 27.2 mmol) was added at room temperature to a suspension of 2-((E)-2-ethoxycarbonylvinyl)-4-trifluoromethylbenzoic acid (2.9 g, 10.1 mmol) in toluene (30 ml). The mixture was stirred at room temperature for 5 min and then heated to 105° C. (bath temperature) within 30 min. At about 70° C., gas evolution commenced. The mixture was stirred at 105° C. for 3 h, then cooled to room temperature, filtered with suction through a kieselguhr layer (2.5×0.5 cm) and washed with toluene, and the filtrate was concentrated by evaporation under reduced pressure. The acid chloride was obtained in the form of a red-brown oil (3.34 g). 2,22-Trifluoroethylamine (1.2 g, 12.1 mmol) and triethylamine (2.58 g, 25.3 mmol) was dissolved at 5° C. in dichloromethane (15 ml), and the acid chloride, dissolved in dichloromethane (20 ml), was added dropwise with ice cooling at such a rate that the temperature was kept between 5° C. and 10° C. The ice bath was then removed and the excess of trifluoroethylamine and a portion of the dichloromethane distilled off under gentle vacuum. Subsequently, the mixture was heated to boiling under reflux for 10 h. After it had been cooled, the mixture was diluted with dichloromethane (50 ml) and extracted twice with aqueous 2N HCl solution (50 ml each time), and the combined organic phases were washed with water (100 ml), dried over Na$_2$SO$_4$ and concentrated under reduced pressure. Ethyl (RS)-(2-(2,2,2-trifluoroethyl)-3-oxo-6-trifluoromethyl-2,3-dihydro-1H-isoindol-1-yl)acetate (3.51 g, 94%) was obtained as a dark brown oil which was purified by crystallization from n-heptane. Mp: 54.5-55.5° C.

$^1$H NMR (400 MHz, CDCl$_3$): δ=1.15 (t, J=7 Hz, 3 H), 2.85 (dd, J$_1$=6 Hz, J$_2$=16 Hz, 1 H), 3.01 (dd, J$_1$=5 Hz, J$_2$=16 Hz), 1 H), 3.83 (m, 1 H), 4.12 (q, J=7 Hz, 2 H), 4.73 (m, 1 H), 5.17 (t, J=6 Hz, 1 H), 7.80 (m, 2 H), 8.01 (d, J=8 Hz, 1 H) ppm.

Combustion analysis: $C_{15}H_{13}F_6NO_3$ (369.27): calc. C, 48.79; H, 3.55; N, 3.79. found C, 48.54; H, 3.49; N, 3.79.

EXAMPLE 5 a) (S)-N-{2-[3-Oxo-2-(2,2,2-trifluoroethyl)-6-trifluoromethyl-2,3-dihydro-1H-isoindol-1-yl]acetyl}guanidine, O,O'-dibenzoyl-L-tartaric acid salt

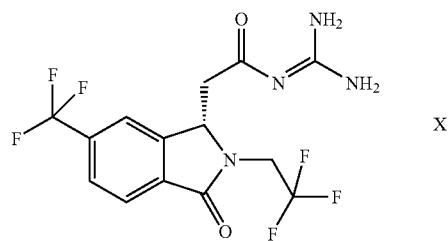

X

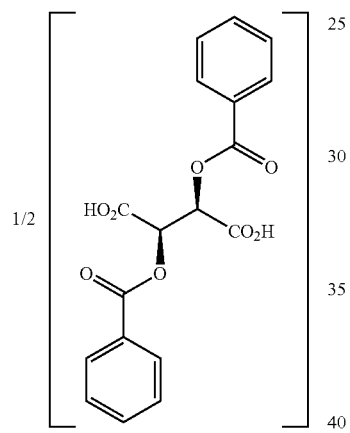

(RS)-N-{2-[3-Oxo-2-(2,2,2-trifluoroethyl)-6-trifluoromethyl-2,3-dihydro-1H-isoindol-1-yl]acetyl}guanidine (inclusion compound with ethyl acetate, content 87.06% by NMR, 44 g, 100 mmol) and O,O'-dibenzoyl-L-tartaric acid (11.2 g, 31 mmol) were initially charged as solids and 2-propanol (500 ml) was added dropwise with stirring. The solids initially dissolved fully, bear a white solid precipitated out. After 30 min, the mixture was heated to 70° C. This again gave an almost clear solution. This was left to cool to room temperature within 4 h and subsequently stirred at this temperature overnight. Afterward, the mixture was stirred at 10° C. for 4 h and subsequently filtered with suction. The residue was washed twice with 2-propanol (100 ml each time) and dried under air. 28.05 g of (S)-N-{2-[3-oxo-2-(2,2,2-trifluoroethyl)-6-trifluoromethyl-2,3-dihydro-1H-isoindol-1-yl]acetyl}guanidine, O,O'-dibenzoyl-L-tartaric acid salt (74% yield based on the (S)-enantiomer), in enantiomeric purity 82% ee by HPLC (Chiracel OD/21, 250×4.6 mm, 50:5:2 n-heptane/ethanol/methanol, 1 ml/min, 30° C. were obtained as colorless crystals. 20 g (14.6 mmol) of these crystals were initially charged and 2-propanol (400 ml) was added dropwise. The mixture was heated to 80° C. with stirring and then left to cool gradually to room temperature. The mixture was stirred at this temperature for a further 2 h and then filtered with suction, and the residue was washed twice with 2-propanol (50 ml each time) and dried under air. 16.3 g (100% yield based on the (S)-enantiomer) of (S)-N-{2-[3-oxo-2-(2, 2,2-trifluoroethyl)-6-trifluoromethyl-2,3-dihydro-1H-isoindol-1-yl]acetyl}guanidine, O,O'-dibenzoyl-L-tartaric acid salt were obtained as colorless crystals, mp: 192-193° C., enantiomeric purity >97% ee by HPLC (conditions as above).

Combustion analysis: $C_{14}H_{12}F_6N_4O_2 \cdot \frac{1}{2}C_{18}H_{14}O_8$ (561.43): calc. C, 49.21; H, 3.41; N, 9.98. found C, 49.17; H, 3.30; N, 9.97.

b) (S)-N-{2-[3-Oxo-2-(2,2,2-trifluoroethyl)-6-trifluoromethyl-2,3-dihydro-1H-isoindol-1-yl]-acetyl}guanidine

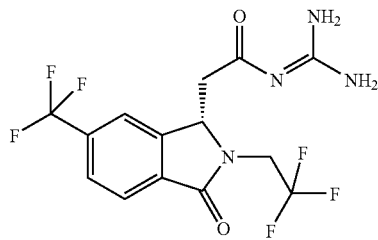

(S)-N-{2-[3-Oxo-2-(2,2,2-trifluoroethyl)-6-trifluoromethyl-2,3-dihydro-1H-isoindol-1-yl]-acetyl}guanidine, O,O'-dibenzoyl-L-tartaric acid salt (113 mg, 0,20 mmol) was dissolved in a mixture of water (1 ml) and ethyl acetate (5 ml) and a solution of $NaHCO_3$ (50 mg) in water (7.5 ml) was added. The mixture was left to stir at room temperature for 16 h and then extracted three times with ethyl acetate (5 ml each time). The combined organic phases were shaken once with a solution of $NaHCO_3$ (50 mg) in water (20 ml) and then with pure water (20 ml), dried over $Na_2SO_4$ and concentrated by evaporation under reduced pressure. 75 mg (97%) of (S)-N-{2-[3-oxo-2-(2,2,2-trifluoroethyl)-6-trifluoromethyl-2,3-dihydro-1H-isoindol-1-yl]-acetyl}guanidine were obtained. The product crystallized from 2-propanol as an inclusion compound with 0.5 equivalent of 2-propanol, mp: 80-82° C. The substance may be recrystallized from ethyl acetate and crystallizes with 0.5 equivalent of ethyl acetate, mp: 121.5-122° C.

Enantiomeric purity >97% by HPLC (Chiracel OD/21, 250·4.6 mm, 4:1 n-heptane/2-propanol, 1 ml/min, 30° C.).

$^1$H NMR (400 MHz, $CDCl_3$): δ=2.54 (dd, $J_1$=8 Hz, $J_2$=16 Hz, 1 H), 3.09 (dd, $J_1$=4 Hz, $J_2$=16 Hz, 1 H), 4.25 (m, 1 H), 4.64 (m, 1 H), 5.18 (m, 1 H), 6.65 (bs, 2 H), 7.75 (bs, 2 H), 7.88 (d, J=8 Hz, 1 H), 7.95 (d, J=8 Hz, 1 H), 8.02 (s, 1 H) ppm.

Combustion analysis (inclusion compound with 0.5 equivalent of 2-propanol):

$C_{14}H_{12}F_6N_4 \cdot \frac{1}{2}C_3H_8O$ (412.32): calc. C, 45.15; H, 3.91; N, 13.59. found C, 45.23; H, 4.27; N, 13.10.

EXAMPLE 6

(RS)-N-{2-[3-Oxo-2-(2,2,2-trifluoroethyl)-6-trifluoromethyl-2,3-dihydro-1H-isoindol-1-yl]acetyl}guanidine by racemization of (R)-N-{2-[3-oxo-2-(2,2,2-trifluoroethyl)-6-trifluoromethyl-2,3-dihydro-1H-isoindol-1-yl]acetyl}guanidine

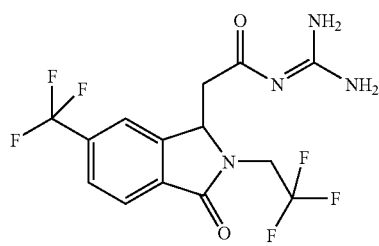

(R)-N-{2-[3-Oxo-2-(2,2,2-trifluoroethyl)-6-trifluoromethyl-2,3-dihydro-1H-isoindol-1-yl]acetyl}guanidine (inclusion compound with 0.5 equivalent of 2-propanol (M=412.3), 43 g, 104 mmol; obtained by concentrating the mother liquor which was obtained in the concentration of (S)-N-{2-[3-oxo-2-(2,2,2-trifluoroethyl)-6-trifluoromethyl-2,3-dihydro-1H-isoindol-1-yl]acetyl}guanidine, O,O'-dibenzoyl-L-tartaric acid salt in example 5a, and treatment with NaHCO$_3$ as described in example 5b)) was dissolved in 2-propanol (1.8 l) and a solution of KOH, 85 percent, 660 mg, 10 mmol) in 2-propanol (400 ml) was added at room temperature with stirring. The mixture was stirred at room temperature for 24 h and then acidified using glacial acetic acid (720 mg, 1.5 ml) and concentrated by evaporation under reduced pressure at a max. bath temperature of 40° C., and the residue was partitioned between water (500 ml) and ethyl acetate (400 ml). The aqueous phase was extracted twice with ethyl acetate (300 ml each time). The combined organic phases were shaken with a solution of NaHCO$_3$ (10 g) in water (500 ml) and then once again with pure water. The organic phase was dried over Na$_2$SO$_4$ and concentrated by evaporation under reduced pressure at a max. bath temperature of 40° C. 39.8 g of (RS)-N-{2-[3-oxo-2-(2,2,2-trifluoroethyl)-6-trifluoromethyl-2,3-dihydro-1H-isoindol-1-yl]acetyl}guanidine, content 87% by NMR, inclusion compound with 0.5 equivalent of ethyl acetate, were obtained as pale yellow crystals, yield: 87%. Mp: 164-166° C. on gentle heating, escape of ethyl acetate from approximately 100° C.

Enantiomeric ratio 49:51 by HPLC (Chiracel OD/21, 250× 4.6 mm, 4:1 n-heptane/2-propanol, 1 mL/min, 30° C.).

EXAMPLE 7

(S)-N-{2-[3-Oxo-2-(2,2,2-trifluoroethyl)-6-trifluoromethyl-2,3-dihydro-1H-isoindol-1-yl]-acetyl}guanidine hydrogenfumarate hydrate

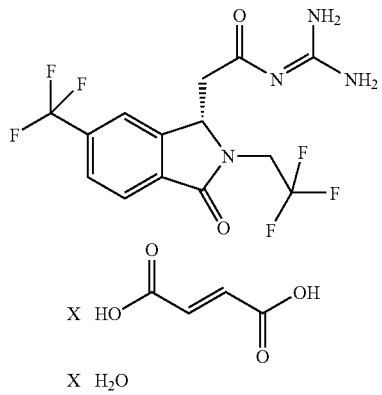

(S)-N-{2-[3-Oxo-2-(2,2,2-trifluoroethyl)-6-trifluoromethyl-2,3-dihydro-1H-isoindol-1-yl]-acetyl}guanidine ☐inclusion compound with 0.5 equivalent of 2-propanol, (M=412.3), 110 g, 266 mmol] was dissolved in dimethoxyethane (2 l) and admixed with fumaric acid solution (0.5M in 9:1 dimethoxyethane/water, 512 ml) and the clear solution formed was concentrated by evaporation under reduced pressure. The residue was taken up with dichloromethane (2 l) and the mixture concentrated again by evaporation under reduced pressure. The residue was suspended in water (1.5 l), filtered with suction at room temperature and dried under air at room temperature overnight. 125.9 g (95%) of (S)-N-{2-[3-oxo-2-(2,2,2-trifluoroethyl)-6-trifluoromethyl-2,3-dihydro-1H-isoindol-1-yl]acetyl}guanidine hydrogenfumarate hydrate were obtained as colorless crystals, mp. 210° C.

Determination of the NHE Inhibition

The inhibitory concentration IC$_{50}$ for NHE-1 inhibition was determined as follows:

The NHE-1 inhibition IC$_{50}$ was determined in an FLIPR assay by measurement of the recovery in pH$_i$ in transfected cell lines which express human NHE-1.

The assay was carried out in an FLIPR (fluorescent imaging plate reader) with black-walled 96-well microtiter plates having clear bases. The transfected cell lines expressing the different NHE subtypes (the parental cell line LAP-1 shows no endogenous NHE activity as a consequence of mutagenesis and subsequent selection) were seeded the preceding day at a density of ~25 000 cells/well.

The growth medium for the transfected cells (Iscove+10% fetal calf serum) additionally contained G418 as a selection antibiotic in order to ensure the presence of the transfected sequences.

The actual assay started with the removal of the growth medium and addition of 100 µl of loading buffer per well (5 µM BCECF-AM [2',7'-bis(carboxyethyl)-5- (and -6-)carboxyfluorescein, acetoxymethyl ester] in 20 mM NH$_4$Cl, 115 mM choline chloride, 1 mM MgCl$_2$, 1 mM CaCl$_2$, 5 mM KCl, 20 mM HEPES, 5 mM glucose; pH 7.4 [adjusted with KOH]). The cells were then incubated at 37° C. for 20 minutes. This incubation led to loading of the cells with the fluorescent dye whose fluorescence intensity depends on pHi, and with NH₄Cl which makes the cells slightly alkaline.

The nonfluorescent dye precursor BCECF-AM is, as the ester, membrane-permeable. Inside the cell, esterases release the actual BCECF dye which is membrane-impermeable.

After this incubation for 20 minutes, the loading buffer which contained NH₄Cl and free BCECF-AM was removed by washing three times in a cell washer (Tecan Columbus) with in each case 400 µl of washing buffer (133.8 mM choline chloride, 4.7 mM KCl, 1.25 mM MgCl₂, 1.25 mM CaCl₂, 0.97 mM K₂HPO₄, 0.23 mM KH₂PO₄, 5 mM HEPES, 5 mM glucose; pH 7.4 [adjusted with KOH]). The residual volume remaining in the wells was 90 µl (50-125 µl possible). This washing step removed the free BCECF-AM and led, as a consequence of the removal of the external NH₄⁺ ions, to intracellular acidification (~pH$_i$ 6.3-6.4).

Since the equilibrium of intracellular NH₄⁺ with NH₃ and H⁺ was disturbed by the removal of the extracellular NH₄⁺ and by the subsequent instantaneous passage of the NH₃ through the cell membrane, the washing process led to H⁺ remaining inside the cells, which was the cause of the intracellular acidification. This may eventually lead to cell death if it persists long enough.

It was important at this point that the washing buffer was sodium-free (<1 mM), since extracellular sodium ions would lead to instantaneous recovery in the pH$_i$ as a result of the activity of the cloned NHE isoforms.

It was likewise important for all buffers used (loading buffer, washing buffer, recovery buffer) not to contain any HCO₃⁻ ions, since the presence of bicarbonate would lead to activation of interfering bicarbonate-dependent pH$_i$ regulatory systems which are present in the parental LAP-1 cell line.

The microtiter plates with the acidified cells were then (up to 20 minutes after the acidification) transferred to the FLIPR. In the FLIPR, the intracellular fluorescent dye was excited by light having a wavelength of 488 nm which was generated by an argon laser, and the measured parameters (laser power, illumination time and aperture of the CCD camera incorporated in the FLIPR) were selected such that the average fluorescence signal per well was between 30 000 and 35 000 relative fluorescence units.

The actual measurement in the FLIPR started with an image being taken by the CCD camera every two seconds under software control. After ten seconds, the recovery of the intracellular pH was initiated by adding 90 µl of recovery buffer (133.8 mM NaCl, 4.7 mM KCl, 1.25 mM MgCl₂, 1.25 mM CaCl₂, 0.97 mM K₂HPO₄, 0.23 mM KH₂PO₄, 10 mM HEPES, 5 mM glucose; pH 7.4 [adjusted with NaOH]) by means of the 96-well pipettor incorporated in the FLIPR.

The positive controls (100% NHE activity) used were wells to which pure recovery buffer had been added, while negative controls (0% NHE activity) received washing buffer.

Recovery buffer with twice the concentration of test substance was added to all other wells. Measurement in the FLIPR ended after 60 measurements (two minutes).

The raw data were exported into the ActivityBase program. This program firstly calculated the NHE activities for each tested substance concentration and, from these, the IC$_{50}$ values for the substances. Since the course of pH$_i$ recovery was not linear over the entire experiment, but rather fell at the end owing to decreasing NHE activity at higher pH$_i$ values, it was important to select, for evaluation of the measurement, the part in which the increase in fluorescence of the positive controls was linear.

| Substance | NHE1 inhibition IC$_{50}$ [nM] |
|---|---|
| (S)-N-{2-[3-Oxo-2-(2,2,2-trifluoroethyl)-6-trifluoromethyl-2,3-dihydro-1H-isoindol-1-yl]acetyl}guanidine | 0.3 |

What claimed is:

1. A process for preparing compounds of the formula I

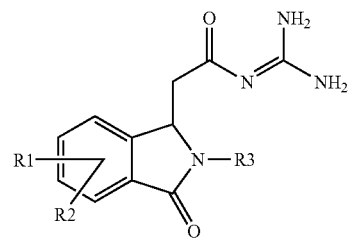

wherein
R1 and R2
are each independently hydrogen, F, Cl, trifluoromethoxy,
2,2,2-trifluoroethoxy, trifluoromethyl, 2,2,2-trifluoroethyl or alkyl having 1, 2, 3 or 4 carbon atoms;
R3 is Alk-R4 or trifluoromethyl;
Alk is alkyl having 1, 2, 3 or 4 carbon atoms;
R4 is hydrogen, trifluoromethyl or cycloalkyl having 3, 4, 5, 6 or 7 carbon atoms;
and salts thereof;
which comprises

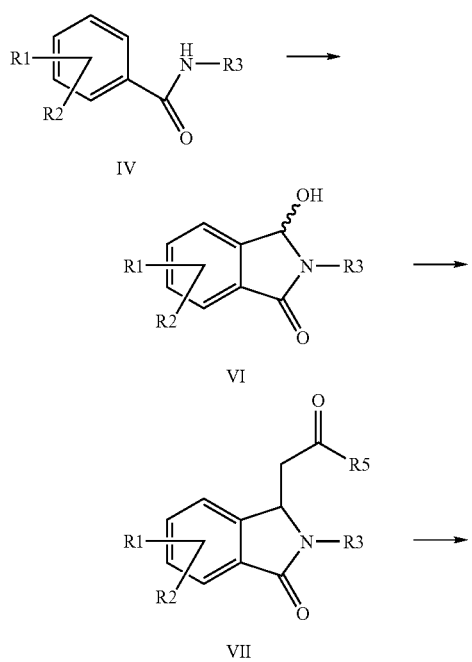

-continued

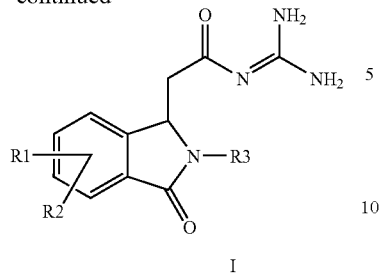

I a) formylating the amide of the formula IV and then cyclizing to the compound of the formula VI,
b) reacting the compound of the formula VI with an alkoxycarbonylmethylene-triphenylphosphorane, with a 1-alkoxy-1-trimethylsiloxyethylene or with a trialkyl phosphonoacetate to give the compound of the formula VII, and
c) reacting the compound of the formula VII with guanidine to give the compound of the formula I,
where, in the compounds of the formulae IV, VI and VII,
R1 to R3 are each as defined in formula I and
R5 is alkoxy having 1, 2, 3 or 4 carbon atoms;
and salts thereof.

2. A process for preparing compounds of the formula I

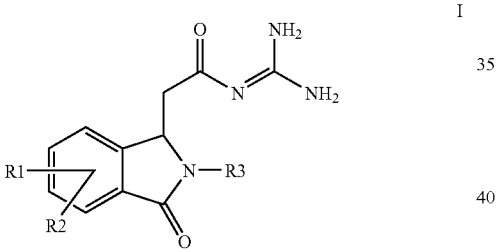

I wherein
R1 and R2
are each independently hydrogen, F, Cl, trifluoromethoxy,
2,2,2-trifluoroethoxy, trifluoromethyl, 2,2,2-trifluoroethyl or alkyk having 1, 2, 3 or 4 carbon atoms;
R3 is Alk-R4 or trifluoromethyl;
Alk is alkyl having 1, 2, 3 or 4 carbon atoms;
R4 is hydrogen, trifluoromethyl or cycloalkyl having 3, 4, 5, 6 or 7 carbon atoms;
and salts thereof;
wherein

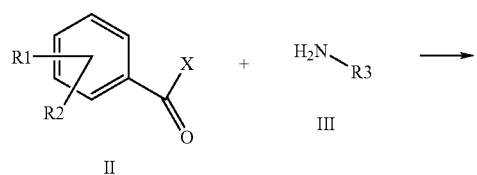

-continued

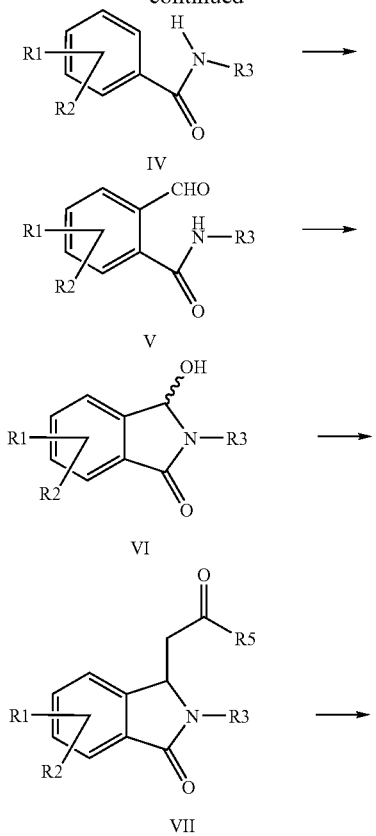

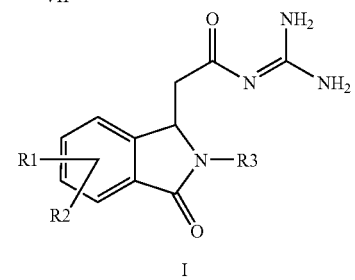

I a) the compound of the formula II is reacted with the amine of the formula III to give the amide of the formula IV,
b) the amide of the formula IV is formylated at the ortho-position to the amide function to give the formyl amide of the formula V,
c) the formyl amide of the formula V is cyclized to the compound of the formula VI,
d) the compound of the formula VI s reacted with an alkoxycarbonylmethylenetriphenylphosphorane, with a 1-alkoxy-1-trimethylsiloxyethylene or with a trialkyl phosphonoacetate to give the compound of the formula VII and
e) the compound of the formula VII is reacted with guanidine to give the compound of the formula I
where, in the compounds of the formulae II, III, IV, V, VI and VII,
R1 to R3 are each as defined in formula I,
R5 is alkoxy having 1, 2, 3 or 4 carbon atoms and
X is Cl, Br, OH or alkoxy having 1, 2, 3 or 4 carbon atoms;
and salts thereof.

3. The process of claim 1 or 2 wherein the process steps are each independently conducted continuously or batchwise.

4. The process of claim 3 wherein the compound of the formula I is defined as N-{2-[3-oxo-2-(2,2,2-trifluoroethyl)-6-trifluoromethyl-2,3-dihydro-1H-isoindol-1-yl]acetyl}guanidine, and pharmaceutically acceptable salts thereof.

5. The process of claims 1 or 2 wherein the compound of the formula I is defined as N-{2-[3-oxo-2-(2,2,2-trifluoroethyl)-6-trifluoromethyl-2,3-dihydro-1H-isoindol-1-yl]acetyl}guanidine, and pharmaceutically acceptable salts thereof.

6. A process for preparing compounds of the formula I

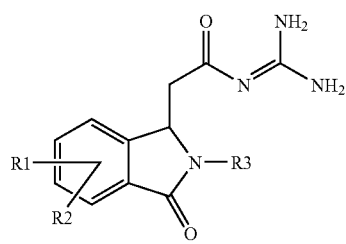

I wherein
R1 and R2
are each independently hydrogen, F, Cl, trifluoromethoxy,
2,2,2-trifluoroethoxy, trifluoromethyl, 2,2,2-trifluoroethyl or alkyl having 1, 2, 3 or 4 carbon atoms;
R3 is Alk-R4 or trifluouomethyl;
Alk is alkyl having 1, 2, 3 or 4 carbon atoms;
R4 is hydrogen, trifluoromethyl or cycloalkyl having 3, 4, 5, 6 or 7 carbon atoms;
and salts thereof;
which comprises

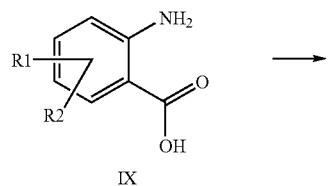

IX

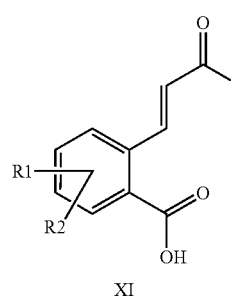

XI

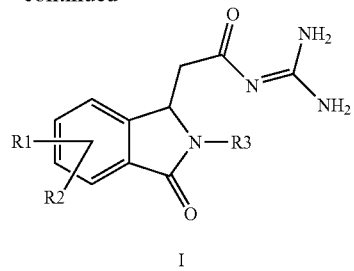

I a) reacting the amine of the formula IX via a diazonium salt with an alkyl acrylate to give the cinnamic acid derivative of the formula XI,
b) reacting the compound of the formula XI with the amine of the formula III and with guanidine to give the acylguanidine of the formula I,
wherein, in the compounds of the formulae III, IX and XI,
R1 to R3 are each as defined in formula I and
R6 is alkoxy having 1, 2, 3 or 4 carbon atoms;
and salts thereof.

7. A process for preparing compounds of the formula I

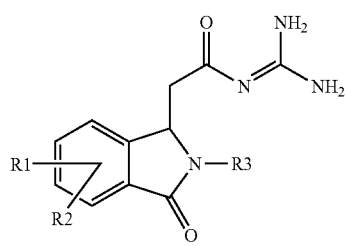

I wherein
R1 and R2
are each independently hydrogen, F, Cl, trifluoromethoxy,
2,2,2-trifluoroethoxy, trifluoromethyl, 2,2,2-trifluoroethyl or alkyl having 1, 2, 3 or 4 carbon atoms;
R3 is Alk-R4 or trifluoromethyl;
Alk is alkyl having 1, 2, 3 or 4 carbon atoms;
R4 is hydrogen, trifluoromethyl or cycloalkyl having 3, 4, 5, 6 or 7 carbon atoms;
and salts thereof;
wherein

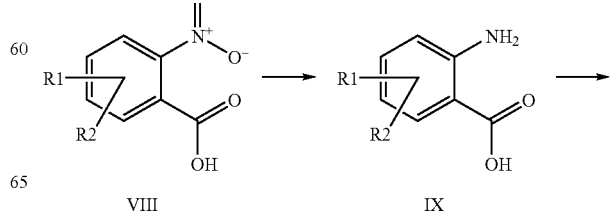

VIII   IX

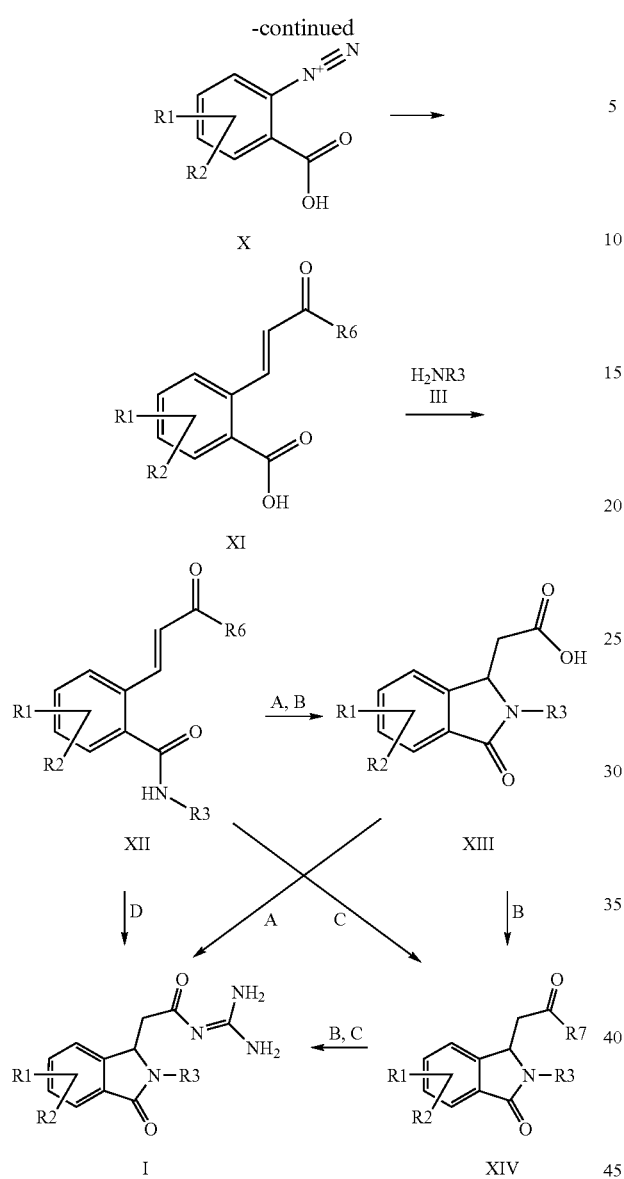

a) the nitro compounds of the formula VIII is converted to the amine of the formula IX, b) the amine of the formula IX is converted to the diazonium salt of the formula X, c) the diazonium salt of the formula X is reacted with an alkyl acrylate to give the cinnamic acid derivative of the formula XI, d) the compound of the formula XI is converted to the amide of the formula XII and e) the compound of the formula XII is converted to the acylguanidine of the formula I, either by converting the compound of the formula XII in the presence of a base to the isoindolone derivative of the formula XIII and subsequently by reaction with guanidine with activation to give the acylguanidine of the formula I (alternative A), or, after formation of the isoindolone derivative of the formula XIII, in the presence of a base, from the compound of the formula XII, by converting the compound of the formula XIII to the ester of the formula XIV and subsequently by reacting with guanidine to give the acylguanidine of the formula I (alternative B), or by converting the compound of the formula XII in the presence of a strong base to the ester of the formula XIV and subsequently by reacting with guanidine to the acylguanidine of the formula I (alternative C), or by directly reacting the compound of the formula XII with guanidine in the presence of a base with simultaneously proceeding guanylation and cyclization to give the isoindolone of the formula I (alternative D), where, in the compounds of the formulae VIII, IX, X, XI, XII, XIII and XIV, R1 to R3 are each as defined in formula I and R6 and R7 are each independently alkoxy having 1, 2, 3 or 4 carbon atoms;

and salts thereof.

8. The process of claim 7 wherein the step of converting the compound of formula XII comprises a) converting the compound of formula XII with in the presence of a base to an isoindolone derivative of formula XIII

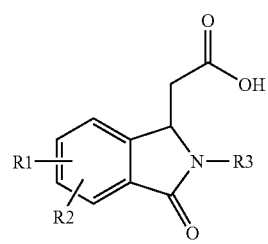

b) and reacting the compound of formula XIII with guanidine with activation to give the compound of formula I.

9. The process of claim 7 wherein the step of converting the compound of formula XII comprises a) converting the compound of formula XII with in the presence of a base to an isoindolone derivative of formula XIII

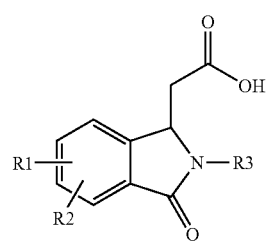

b) converting the compound of formula XIII to the ester of formula XIV

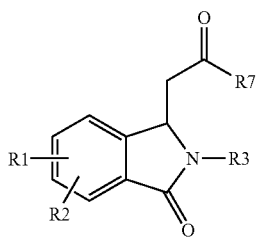

wherein R7 is alkoxy having 1, 2, 3 or 4 carbon atoms, and
c) reacting the compound of formula XIV with guanidine to give the compound of formula I.

10. The process of claim 7 wherein the step of converting the compound of formula XII comprises
   a) converting the compound of formula XII with in the presence of a strong base to an ester of formula XIV

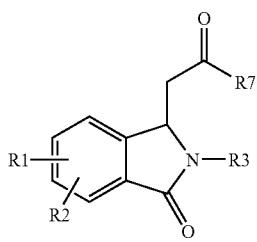

wherein R7 is alkoxy having 1, 2, 3 or 4 carbon atoms, and
b) reacting the compound of formula XIV with guanidine to give the compound of formula I.

11. The process of claim 7 wherein the step of converting the compound of formula XII comprises reacting the compound of formula XII with guanidine in the presence of a base with simultaneous guanylation and cyclization to give the compound of formula I.

12. The process of claim 7 wherein process steps d) and e) are carried out in a one-pot process.

13. The process of claim 7 wherein the steps are each independently conducted continuously or batchwise.

14. The process of claim 6 wherein the compound of the formula XI is defined as having a formula that when reacted with guanidine provides N-{2-[3-oxo-2-(2,2,2-trifluoroethyl)-6-trifluoroethyl-2,3-dihydro-1H-isoindol-1-yl]acetyl}guanidine, and pharmaceutically acceptable salts thereof.

15. A compound of the formula XII

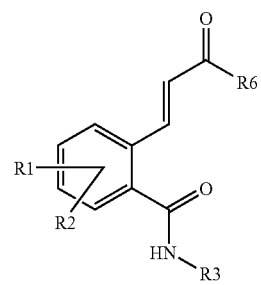

wherein
R1 and R2
   are each independently hydrogen, F, Cl, trifluoromethoxy,
   2,2,2-trifluoroethoxy, trifluoromethyl, 2,2,2-trifluoroethyl or alkyl having 1, 2, 3 or 4 carbon atoms;
R3 is Alk-R4, trifluoromethyl, wherein Alk is alkyl having 1, 2, 3 or 4 carbon atoms, and R4 is hydrogen, trifluoromethyl or cycloalkyl having 3, 4, 5, 6 or 7 carbon atoms;
R6 is alkoxy having 1, 2, 3 or 4 carbon atoms;
and salts thereof.

16. A process for isolating compounds of the formula Ia and Ib

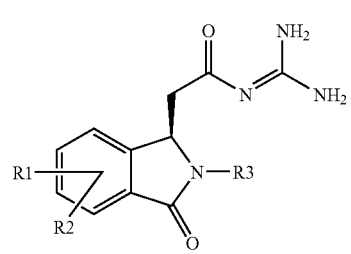

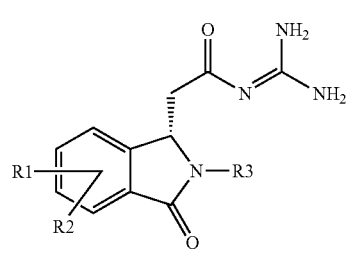

wherein
R1 and R2
   are each independently hydrogen, F, Cl, trifluoromethoxy,
   2,2,2-trifluoroethoxy, trifluoromethyl, 2,2,2-trifluoroethyl or alkyl having 1, 2, 3 or 4 carbon atoms;
R3 is Alk-R4 or trifluoromethyl;
Alk is alkyl having 1, 2, 3 or 4 carbon atoms;
R4 is hydrogen, trifluoromethyl or cycloalkyl having 3, 4, 5, 6 or 7 carbon atoms;
and salts thereof;
which comprises

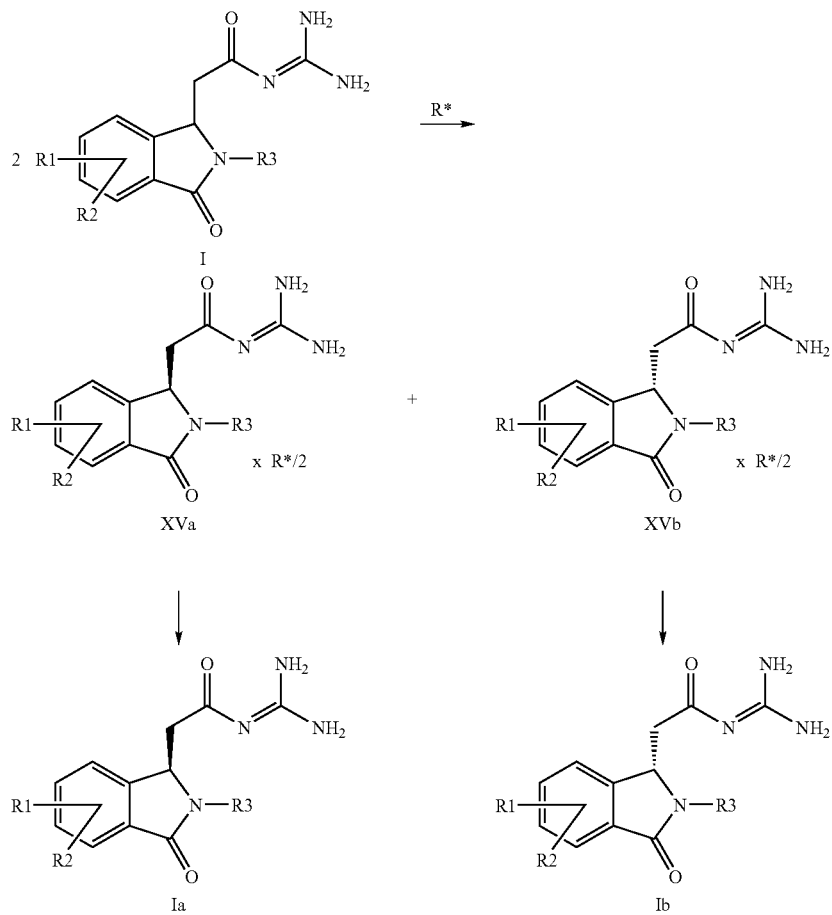

Scheme 5 a) converting the compound of the formula I to salts of a 2,3-O-acylated D- or L-tartaric acid and obtaining the two salts of the formulae XVa and XVb separately by crystallization, and
b) releasing the free bases of the formulae Ia and Ib from the two salts of the formulae XVa and XVb respectively, where, in the compounds of the formulae I, XVa and XVb. R1 to R3 are each as defined in the formulae Ia and Ib R* is

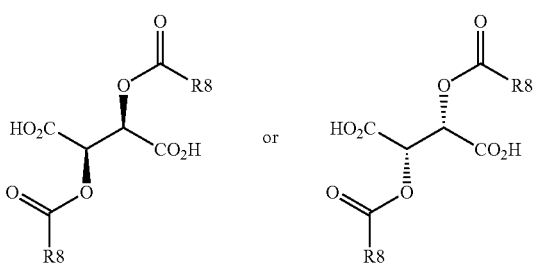

R8 is alkyl having 1, 2, 3, 4, 5 or 6 carbon atoms or phenyl which is unsubstituted or substituted by 1, 2 or 3 substituents from the group of F, Cl, Br, I, alkyl having 1, 2, 3 or 4 carbon atoms or alkoxy having 1, 2, 3 or 4 carbon atoms.

17. The process of claim 16 further comprising a step where either formula Ia compound, or a formula Ib compound is racemized.

18. The process of claim 16 wherein the compounds of the formulae Ia and Ib are (R)-N-{2-[3-oxo-2-(2,2,2-trifluoroethyl)-6-trifluoromethyl-2,3-dihydro-1H-isoindol-1-yl]acetyl}guanidine and (S)-N-{2-[3-oxo-2-(2,2,2-trifluoroethyl)-6-trifluoromethyl-2,3-dihydro-1H-isoindol-1-yl]acetyl}guanidine.

* * * * *